US010509024B2

(12) United States Patent
Zelmanovic et al.

(10) Patent No.: US 10,509,024 B2
(45) Date of Patent: Dec. 17, 2019

(54) SYSTEM AND METHOD FOR DISTINGUISHING BLOOD COMPONENTS

(71) Applicant: LabThroughput LLC, Monsey, NY (US)

(72) Inventors: David Zelmanovic, Monsey, NY (US); John Roche, San Francisco, CA (US)

(73) Assignee: LABTHROUGHPUT LLC, Monsey, NY (US)

(*) Notice: Subject to any disclaimer, the term of this patent is extended or adjusted under 35 U.S.C. 154(b) by 119 days.

(21) Appl. No.: 15/585,900

(22) Filed: May 3, 2017

(65) Prior Publication Data

US 2017/0322198 A1 Nov. 9, 2017

Related U.S. Application Data

(60) Provisional application No. 62/331,829, filed on May 4, 2016.

(51) Int. Cl.
| | |
|---|---|
| *G01N 15/10* | (2006.01) |
| *G01N 33/49* | (2006.01) |
| *G01N 15/06* | (2006.01) |
| *G01N 15/14* | (2006.01) |
| *G01N 21/53* | (2006.01) |
| *G01N 21/59* | (2006.01) |
| *G01N 15/00* | (2006.01) |

(52) U.S. Cl.
CPC ......... *G01N 33/4915* (2013.01); *G01N 15/06* (2013.01); *G01N 15/1436* (2013.01); *G01N 21/53* (2013.01); *G01N 21/59* (2013.01); *G01N 2015/008* (2013.01); *G01N 2015/0073* (2013.01); *G01N 2015/0084* (2013.01); *G01N 2015/0693* (2013.01); *G01N 2015/1006* (2013.01)

(58) Field of Classification Search
CPC combination set(s) only.
See application file for complete search history.

(56) References Cited

U.S. PATENT DOCUMENTS

| | | | |
|---|---|---|---|
| 5,438,003 A | 8/1995 | Colella et al. | |
| 5,817,519 A | 10/1998 | Zelmanovic et al. | |
| 6,524,858 B1 | 2/2003 | Zelmanovic et al. | |
| 8,906,308 B2 | 12/2014 | Krockenberger et al. | |
| 8,906,309 B2 | 12/2014 | Krockenberger et al. | |
| 2010/0273168 A1* | 10/2010 | Krockenberger | G01N 15/00 435/6.12 |
| 2011/0124031 A1* | 5/2011 | Hazen | G01N 33/6893 435/29 |
| 2014/0295488 A1* | 10/2014 | Konishi | G01N 21/49 435/34 |

OTHER PUBLICATIONS

Lei Bi, et al., "Modeling of light scattering by biconcave and deformed red blood cells with the invariant imbedding T-matrix method", Journal of Biomedical Optics, May 2013, vol. 18(5), pp. 055001-1-055001-13, http://www.biomedicaloptics.spiedigitallibrary.org/, on Mar. 4, 2016.

Dizem Arifler, et al., "Light scattering from normal and dysplastic cervical cells at different epithelial depths: finite-difference time-domain modeling with a perfectly matched layer boundary condition", Journal of Biomedical Optics, Jul. 2013, vol. 8, No. 3, pp. 484-494, https://www.spiedigitallibrary.org/journals/Journal-of-Biomedical-Optics on Oct. 3, 2017.

Akihisa Nonoyama, "Using Multiwavelength UV-Visible Spectroscopy for the Characterization of Red Blood Cells: An investigation of Hypochromism", A dissertation submitted in partial fulfillment of the requirements for the degree of Doctor of Philosophy, Department of Chemistry, College of Arts and Sciences, University of South Florida, © Copyright 2004, Akihisa Nonoyama, pp. 1-256.

Annika M. K. Nilsson et al., "T-matrix computations of light scattering by red blood cells", Applied Optics, vol. 37, No. 13, May 1, 1998, pp. 2735-2748.

Andrew Dunn, et al., "Three-Dimensional Computation of Light Scattering From Cells", IEEE Journal of Selected Topics in Quantum Electronics, vol. 2, No. 4, Dec. 1996, pp. 898-905, © 1996 IEEE.

Dongwoo Jang, et al., "Study on Light Scattering to Estimate the White Blood Cell Count", New Physics: Sae Mulli, vol. 63, No. 10, Oct. 2013, pp. 1155-1159.

Martin Hammer et al., "Single scattering by red blood cells", Applied Optics, vol. 37, No. 31, Nov. 1, 1998, pp. 7410-7418.

Jiajie Wang, et al., "Shaped beam scattering from a single lymphocyte cell by generalized Lorenz-Mie theory", ScienceDirect, Journal of Quantitative Spectroscopy and Radiative Transfer 133, Jan. 2014, pp. 72-80, www.elsevier.com/locate/jqsrt.

Oleksiy Sydoruk, et al., "Refractive index of solutions of human hemoglobin from the near-infrared to the ultraviolet range: Kramers-Kronig analysis", Journal of Biomedical Optics, vol. 17(11), Nov. 2012, pp. 115002-1-115002-6, http://biomedicaloptics.spiedigitallibrary.org/on Nov. 5, 2012.

(Continued)

*Primary Examiner* — Paul S Hyun
(74) *Attorney, Agent, or Firm* — Cowan, Liebowitz & Latman, P.C.; Mark Montague; Brian R. Yolk

(57) ABSTRACT

A method for measuring concentrations of blood cell components is provided. The method comprises: obtaining a blood sample from a subject, the blood sample comprising red blood cells (RBCs), white blood cells (WBCs), and platelets (PLTs); mixing the blood sample with a non-lysing aqueous solution to form a sample mixture comprising a predetermined tonicity; passing the sample mixture through a flow cell; emitting light towards the flow cell; measuring an amount of light absorbed by the RBCs; measuring an amount of light scattered by WBCs, and PLTs; determining a concentration of each of the RBCs, WBCs, and PLTs present in the sample mixture from the measured amount of light absorbed by the RBCs and scattered by the WBCs and PLTs.

27 Claims, 44 Drawing Sheets

(56) References Cited

OTHER PUBLICATIONS

Matti Kinnunen, et al., "Overview of single-cell elastic light scattering techniques", Journal of Biomedical Optics vol. 20(5), 051040 (May 2015), pp. 051040-1-051040-11, http://biomedicaloptics.spiedigitallibrary.org/ on Mar. 8, 2017.

Andre Roggan, et al., "Optical Properties of Circulating Human Blood in the Wavelength Range 400-2500 NM", Journal of Biomedical Optics vol. 4, No. 1, 36-46 (Jan. 1999).

Anders Karlsson, et al., "Numerical Simulations of Light Scattering by Red Blood Cells", IEEE Transactions on Biomedical Engineering, vol. 52, No. 1, Jan. 2005, Copyright 2005 IEEE, pp. 13-18.

S. Saltsberger, et al., "Multilayer Mie Scattering Model for Investigation of Intracellular Structural Changes in the Nucleolus and Cytoplasm", Hindawi Publishing Corporation, International Journal of Optics, vol. 2012, Article ID 947607, 9 pages, doi:10.1155/2012/947607, pp. 1-9.

Philippe Nerin, "HORIBA Medical in Europe: Evolution of Technologies for White Blood Cell Differential at HORIBA Medical", Readout, English Edition No. 39, Sep. 2012, pp. 12-33.

S. De Boever, et al., "Flow cytomeric differentiation of avian leukocytes and analysis of their intracellular cytokine expression", Avian Pathology, Feb. 2010, 39:1, pp. 41-46, ISSN: 0307-9457 (Print) 1465-3338 (Online) Journal homepage: http://www.tandfonline.com/loi/cavp20.

Dakota Watson, et al., "Elastic Light Scattering from Single Cells: Orientational Dynamics in Optical Trap", Biophysical Journal, vol. 87(2), Aug. 2004, pp. 1298-1306.

Antoon Georgius Hoekstra "Computer Simulations of Elastic Light Scattering", Implementation and Applications, Feb. 11, 1994, Printed by CopyPrint 2000, Enschede, the Netherlands, pp. 1-191.

Tuan Vo-Dinh, "Biomedical Photonics Handbook", Oak Ridge National Laboratory, Oak Ridge, Tennessee, CRC Press, Feb. 2003, pp. 1-1787.

Hiroyuki Horiuchi, et al., "A Monoclonal Antibody against Chicken Thrombocytes Reacts with the Cells of Thrombocyte Lineage", Laboratory of Immunobiology, Department of Molecular and Applied Biosciences, Hiroshima University, 1-4-4 Kagamiyama, Higashi-Hiroshima 739-8528, Japan, J. Vet. Med. Sci. 66(3), pp. 243-250, 2004.

Jeremy D. Wilson, et al., "Light Scattering from Intact Cells Reports Oxidative-Stress-Induced Mitochondrial Swelling", Biophysical Journal, vol. 88, Apr. 2005, Biophysical Journal 88(4), pp. 2929-2938.

Rebekah Drezek, et al., "Light scattering from cells: finite-difference time-domain simulations and goniometric measurements", Applied Optics, vol. 38, No. 16, Jun. 1, 1999, pp. 3651-3661.

D.Y. Orlova, et al., "Light scattering by neutrophils: Model, simulation, and experiment", Journal of Biomedical Optics 13(5), 054057 (Sep./Oct. 2008), pp. 054057-1-054057-7, http://hdl.handle.net/11245/1.296236.

D.I. Strokotov, et al., "Is there a difference between T- and B-lymphocyte morphology?", Journal of Biomedical Optics 14(6), 064036 (Nov./Dec. 2009), pp. 064036-1-064036-12, http://hdl.handle.net/11245/1.312437.

Gennady I. Ruban, et al., "Investigation of morphometric parameters for granulocytes and lymphocytes as applied to a solution of direct and inverse light-scattering problems", Journal of Biomedical Optics 12(4), 044017 (Jul./Aug. 2007), pp. 044017-1-044017-12, http://www.biomedicaloptics.spiedigitallibrary.org/ on Feb. 21, 2016.

Caigen Liu, et al., "3-D simulation of light scattering from biological cells and cell differentiation", Journal of Biomedical Optics 10(1), 014007 (Jan./Feb. 2005), pp. 014007-1-014007-12, https://www.spiedigitallibrary.org/journals/Journal-of-Biomedical-Optics on Oct. 3, 2017.

Tadaaki Moritomo, et al., "A New Method for Counting of Quail Leukocytes by Flow Cytometry", Laboratory of Fish Pathology, Department of Veterinary Medicine, Nihon University, 1866 Kameino, Fujisawa, Kanagawa 282-8510, Japan, J. Vet. Med. Sci. (64(12), 2002, pp. 1149-1151.

* cited by examiner

| Dia. (μ) | Computed Signal (AU) | Actual Mean Channel | Theoretical Mean Channel | Baseline Restore (-1200 channels) | |
|---|---|---|---|---|---|
| | | | | Actual Mean Channel | Theoretical Mean Channel |
| 3.2 | 5.2 | 3175 | 2179 | 1875 | 1942 |
| 5.0 | 13.5 | 6900 | 5701 | 5600 | 5079 |
| 7.0 | 26.1 | 11000 | 11000 | 9800 | 9800 |

FIG. 11

| Volume (fl) | Radius (microns) | MCHC (g/L) | Absorption Cross Section | MCH (pg) | Calculated MCH | Calculated Minus Real MCH | % Delta |
|---|---|---|---|---|---|---|---|
| 15 | 1.53 | 230 | 3.21 | 3.5 | 4.8 | 1.4 | 28.2 |
| 30 | 1.93 | 230 | 6.02 | 6.9 | 8.1 | 1.2 | 14.3 |
| 45 | 2.20 | 230 | 8.52 | 10.4 | 11.2 | 0.9 | 7.9 |
| 60 | 2.43 | 230 | 11.05 | 13.8 | 14.7 | 0.9 | 6.3 |
| 75 | 2.61 | 230 | 13.30 | 17.3 | 18.1 | 0.8 | 4.5 |
| 90 | 2.78 | 230 | 15.64 | 20.7 | 21.8 | 1.1 | 4.9 |
| 105 | 2.92 | 230 | 17.74 | 24.2 | 25.3 | 1.1 | 4.4 |
| 120 | 3.06 | 230 | 19.97 | 27.6 | 29.2 | 1.6 | 5.5 |
| 135 | 3.18 | 230 | 22.06 | 31.1 | 33.1 | 2.0 | 6.1 |
| 150 | 3.29 | 230 | 23.97 | 34.5 | 36.8 | 2.3 | 6.2 |
| 165 | 3.40 | 230 | 26.02 | 38.0 | 40.9 | 3.0 | 7.3 |
| 180 | 3.50 | 230 | 27.96 | 41.4 | 45.0 | 3.6 | 8.1 |
| 195 | 3.59 | 230 | 29.77 | 44.9 | 49.0 | 4.2 | 8.5 |
| 210 | 3.68 | 230 | 31.65 | 48.3 | 53.3 | 5.0 | 9.3 |
| 225 | 3.77 | 230 | 33.58 | 51.8 | 57.8 | 6.1 | 10.5 |
| 240 | 3.85 | 230 | 35.36 | 55.2 | 62.1 | 6.9 | 11.1 |
| 255 | 3.93 | 230 | 37.18 | 58.7 | 66.7 | 8.0 | 12.1 |
| 270 | 4.00 | 230 | 38.81 | 62.1 | 70.9 | 8.8 | 12.4 |
| 285 | 4.08 | 230 | 40.72 | 65.6 | 76.0 | 10.4 | 13.7 |
| 300 | 4.15 | 230 | 42.43 | 69.0 | 80.7 | 11.7 | 14.4 |
| 15 | 1.53 | 297.5 | 3.90 | 4.5 | 5.6 | 1.1 | 19.8 |
| 30 | 1.93 | 297.5 | 7.18 | 8.9 | 9.5 | 0.6 | 6.0 |
| 45 | 2.20 | 297.5 | 10.06 | 13.4 | 13.3 | -0.1 | 0.5 |
| 60 | 2.43 | 297.5 | 12.94 | 17.9 | 17.5 | -0.3 | 2.0 |
| 75 | 2.61 | 297.5 | 15.47 | 22.3 | 21.5 | -0.8 | 3.9 |
| 90 | 2.78 | 297.5 | 18.10 | 26.8 | 25.9 | -0.9 | 3.5 |
| 105 | 2.92 | 297.5 | 20.42 | 31.2 | 30.0 | -1.2 | 4.1 |
| 120 | 3.06 | 297.5 | 22.89 | 35.7 | 34.7 | -1.0 | 2.9 |
| 135 | 3.18 | 297.5 | 25.13 | 40.2 | 39.1 | -1.0 | 2.7 |
| 150 | 3.29 | 297.5 | 27.28 | 44.6 | 43.6 | -1.0 | 2.4 |
| 165 | 3.40 | 297.5 | 29.52 | 49.1 | 48.5 | -0.6 | 1.3 |
| 180 | 3.50 | 297.5 | 31.64 | 53.6 | 53.2 | -0.3 | 0.6 |
| 195 | 3.59 | 297.5 | 33.60 | 58.0 | 57.9 | -0.1 | 0.2 |
| 210 | 3.68 | 297.5 | 35.63 | 62.5 | 62.8 | 0.3 | 0.5 |
| 225 | 3.77 | 297.5 | 37.72 | 66.9 | 68.1 | 1.1 | 1.7 |
| 240 | 3.85 | 297.5 | 39.63 | 71.4 | 73.1 | 1.7 | 2.3 |
| 255 | 3.93 | 297.5 | 41.58 | 75.9 | 78.3 | 2.5 | 3.1 |
| 270 | 4.00 | 297.5 | 43.33 | 80.3 | 83.2 | 2.8 | 3.4 |
| 285 | 4.08 | 297.5 | 45.38 | 84.8 | 89.0 | 4.2 | 4.7 |
| 300 | 4.15 | 297.5 | 47.20 | 89.3 | 94.4 | 5.1 | 5.4 |

FIG. 34

| Volume (fl) | Radius (microns) | MCHC (g/L) | Absorption Cross Section | MCH (pg) | Calculated MCH | Calculated Minus Real MCH | % Delta |
|---|---|---|---|---|---|---|---|
| 15 | 1.53 | 365 | 4.49 | 5.5 | 6.2 | 0.8 | 12.3 |
| 30 | 1.93 | 365 | 8.15 | 11.0 | 10.8 | -0.2 | 1.9 |
| 45 | 2.20 | 365 | 11.31 | 16.4 | 15.1 | -1.3 | 8.8 |
| 60 | 2.43 | 365 | 14.45 | 21.9 | 19.8 | -2.1 | 10.4 |
| 75 | 2.61 | 365 | 17.18 | 27.4 | 24.3 | -3.1 | 12.6 |
| 90 | 2.78 | 365 | 20.00 | 32.9 | 29.2 | -3.6 | 12.3 |
| 105 | 2.92 | 365 | 22.48 | 38.3 | 33.9 | -4.5 | 13.1 |
| 120 | 3.06 | 365 | 25.10 | 43.8 | 39.1 | -4.7 | 12.1 |
| 135 | 3.18 | 365 | 27.47 | 49.3 | 44.0 | -5.3 | 12.0 |
| 150 | 3.29 | 365 | 29.74 | 54.8 | 48.9 | -5.8 | 11.9 |
| 165 | 3.40 | 365 | 32.10 | 60.2 | 54.3 | -5.9 | 10.9 |
| 180 | 3.50 | 365 | 34.31 | 65.7 | 59.6 | -6.1 | 10.3 |
| 195 | 3.59 | 365 | 36.37 | 71.2 | 64.7 | -6.5 | 10.1 |
| 210 | 3.68 | 365 | 38.49 | 76.7 | 70.1 | -6.6 | 9.4 |
| 225 | 3.77 | 365 | 40.67 | 82.1 | 75.8 | -6.3 | 8.3 |
| 240 | 3.85 | 365 | 42.65 | 87.6 | 81.3 | -6.3 | 7.8 |
| 255 | 3.93 | 365 | 44.68 | 93.1 | 87.0 | -6.1 | 7.0 |
| 270 | 4.00 | 365 | 46.49 | 98.6 | 92.3 | -6.3 | 6.8 |
| 285 | 4.08 | 365 | 48.61 | 104.0 | 98.6 | -5.5 | 5.5 |
| 300 | 4.15 | 365 | 50.49 | 109.5 | 104.4 | -5.1 | 4.9 |

FIG. 35

| Volume (fl) | Radius (microns) | MCHC (g/L) | Absorption Cross Section | MCH (pg) | Calculated MCH | Calculated Minus Real MCH | % Delta |
|---|---|---|---|---|---|---|---|
| 15 | 1.53 | 230 | 3.21 | 3.5 | 4.8 | 1.4 | 28.2 |
| 30 | 1.93 | 230 | 6.02 | 6.9 | 8.1 | 1.2 | 14.3 |
| 45 | 2.20 | 230 | 8.52 | 10.4 | 11.2 | 0.9 | 7.9 |
| 60 | 2.43 | 230 | 11.05 | 13.8 | 14.7 | 0.9 | 6.3 |
| 75 | 2.61 | 230 | 13.30 | 17.3 | 18.1 | 0.8 | 4.5 |
| 90 | 2.78 | 230 | 15.64 | 20.7 | 21.8 | 1.1 | 4.9 |
| 105 | 2.92 | 230 | 17.74 | 24.2 | 25.3 | 1.1 | 4.4 |
| 120 | 3.06 | 230 | 19.97 | 27.6 | 29.2 | 1.6 | 5.5 |
| 15 | 1.53 | 297.5 | 3.90 | 4.5 | 5.6 | 1.1 | 19.8 |
| 30 | 1.93 | 297.5 | 7.18 | 8.9 | 9.5 | 0.6 | 6.0 |
| 45 | 2.20 | 297.5 | 10.06 | 13.4 | 13.3 | -0.1 | 0.5 |
| 60 | 2.43 | 297.5 | 12.94 | 17.9 | 17.5 | -0.3 | 2.0 |
| 75 | 2.61 | 297.5 | 15.47 | 22.3 | 21.5 | -0.8 | 3.9 |
| 90 | 2.78 | 297.5 | 18.10 | 26.8 | 25.9 | -0.9 | 3.5 |
| 105 | 2.92 | 297.5 | 20.42 | 31.2 | 30.0 | -1.2 | 4.1 |
| 120 | 3.06 | 297.5 | 22.89 | 35.7 | 34.7 | -1.0 | 2.9 |
| 15 | 1.53 | 365 | 4.49 | 5.5 | 6.2 | 0.8 | 12.3 |
| 30 | 1.93 | 365 | 8.15 | 11.0 | 10.8 | -0.2 | 1.9 |
| 45 | 2.20 | 365 | 11.31 | 16.4 | 15.1 | -1.3 | 8.8 |
| 60 | 2.43 | 365 | 14.45 | 21.9 | 19.8 | -2.1 | 10.4 |
| 75 | 2.61 | 365 | 17.18 | 27.4 | 24.3 | -3.1 | 12.6 |
| 90 | 2.78 | 365 | 20.00 | 32.9 | 29.2 | -3.6 | 12.3 |
| 105 | 2.92 | 365 | 22.48 | 38.3 | 33.9 | -4.5 | 13.1 |
| 120 | 3.06 | 365 | 25.10 | 43.8 | 39.1 | -4.7 | 12.1 |

FIG. 36

|  | X | Y | Units |
|---|---|---|---|
| $M^2$ | 1.25 | 1.15 | mm |
| Beam Diameter | 0.96 | 1.80 | mm |
| Waist Location | 0.03 | -0.15 | Meters |
| Divergence | 0.67 | 0.33 | mrad |
| Astigmatism(Zoy-Zox)/Zrr |  | -6.41 | % |
| Waist Asymmetry(2Woy/2Wox) |  | 1.889 |  |
| Div. Asymmetry Thetay/Thetax |  | 0.488 |  |

FIG. 40

SYSTEM AND METHOD FOR DISTINGUISHING BLOOD COMPONENTS

CROSS REFERENCE TO RELATED APPLICATION

This application claims priority to U.S. Provisional Application No. 62/331,829, filed on May 4, 2016, the entire content of which is incorporated herein by reference.

BACKGROUND OF THE INVENTION

1. Field of the Invention

The present invention relates generally to a flow optical system and method for distinguishing blood components, and in particular, a flow optical system and method for distinguishing red blood cells, including nucleated red blood cells, from white blood cells and platelets.

2. Description of the Related Art

Distinguishing red blood cells (RBC) from both white blood cells (WBC) and platelets (PLT) in order to determine complete blood counts (CBC) and white blood cell differential counts (Diff) for whole blood samples using automated instrumentation currently involves multiple separate analyses. One analytical cycle provides information about RBC and PLT, including cell counts as well as certain indices such as MCV, RDW, and MPV. In another analysis, information about WBC, including total cell counts and differential counts, is determined. A third analysis, referred to as hemoglobinometry, may be performed to determine overall hemoglobin concentration. Information determined by hemoglobinometry is combined with information from the RBC/PLT analysis to obtain values for additional indices such as MCHC and MCH.

Also, to enumerate reticulocytes, a fourth analytic cycle may be performed, although this fourth analysis can be incorporated into the RBC/PLT analysis using suitable reagents. Separate analytical cycles are performed for reticulocyte determinations because of the high cost of reticulocyte reagents and because reticulocyte analyses are typically performed on less than 10% of samples undergoing CBC/Diff analysis. Finally, a fifth analytical cycle may be performed to obtain accurate nucleated red blood cell (NRBC) counts in mammalian samples. If nucleated red blood cells are not distinguished from white blood cells, then white blood cell counts will be overestimated by the number of nucleated red cells.

U.S. Pat. No. 8,906,309 discloses a method for counting of RBCs, WBCs, and PLTs that measures RBC light scattering. This method relies on differences in scattering intensity between RBCs and WBCs. However, this method fails for species with RBCs as large as WBCs. These include chordate species, such as avian and reptilian, and other species whose RBCs are as large as, or larger, than lymphocytic WBCs, or human samples with large RBCs and small lymphocytes, where mutual interference can occur. Further, this method does not provide hemoglobin content information based on direct measurement.

Numerous other methods exist that require the use of expensive fluorescent dyes which in turn require the use of expensive photomultiplier tube (PMT) detectors, while other methods require the use of expensive monoclonal antibodies coupled to fluorescent dyes.

SUMMARY OF THE INVENTION

According to embodiments of the present invention, a method for measuring concentrations of blood cell components is provided. The method comprises: obtaining a blood sample from a subject, the blood sample comprising red blood cells (RBCs), white blood cells (WBCs), and platelets (PLTs); mixing the blood sample with a non-lysing aqueous solution to form a sample mixture comprising a predetermined tonicity; passing the sample mixture through a flow cell; emitting light towards the flow cell; measuring an amount of light absorbed by the RBCs; measuring an amount of light scattered by WBCs, and PLTs; determining a concentration of each of the RBCs, WBCs, and PLTs present in the sample mixture from the measured amount of light absorbed by the RBCs and scattered by the WBCs and PLTs.

According to further embodiments: the method comprises measuring an amount of light side-scattered by the RBCs, WBCs, and PLTs and resolving overlap between the amount of light absorbed by the RBCs and the amount of light scattered by the WBCs, and PLTs from the amount of light side-scattered by the RBCs, WBCs, and PLTs in order to determine the concentration of each of the RBCs, WBCs, and PLTs; the method comprises measuring an amount of light side-scattered by the RBCs, WBCs, and PLTs and distinguishing between the concentrations of RBCs, WBCs and PLTs from the amount of light absorbed by the RBCs, the amount of light scattered by the WBCs, and PLTs, and the amount of light side-scattered by the RBCs, WBCs, and PLTs; the subject is a human and the blood sample comprises human red blood cells (HRBCs), human white blood cells (HWBCs), and human platelets (HPLTs), the method further comprising distinguishing between the HRBCs and the HPLTs across a human physiologic range of RBC sizes of about 15 fL to about 180 fL and a human physiologic range of PLT sizes of about 1 fL to about 60 fL; the method comprises distinguishing between the HRBCs and the HPLTs across a human physiologic range of component concentrations of about 1000/microliter to about 1,500,000/microliter of PLTs and of about 250,000/microliter to about 7,000,000/microliter of RBCs; the amount of light absorbed by the RBCs is measured with the amount of light scattered by the WBCs; the RBCs are present in the sample mixture when the amount of light scattered by the WBCs is measured; the blood sample comprises nucleated red blood cells (NRBCs); the method comprises measuring an amount of light absorbed by the NRBCs and determining a concentration of the NRBCs present in the sample mixture from the measured amount of light absorbed by the NRBCs and scattered by the WBCs and PLTs; the subject is a chordate; the sample mixture comprises at least one surfactant comprising Brij 35 and sodium dodecyl sulfate to sphere the RBCs; the non-lysing aqueous solution converts oxyhemoglobin to methemoglobin present in the sample mixture while substantially maintaining the predetermined tonicity; the non-lysing aqueous solution comprises a reagent that converts oxyhemoglobin to methemoglobin; the predetermined tonicity is 260-330 milliosmolar (mOsm); the method comprises determining a concentration of hemoglobin (HGB) in the blood sample from the amount of light absorbed by the RBCs; the method comprises distinguishing between the concentrations of RBCs, WBCs and PLTs by the amount of light absorbed by the RBCs, scattered by WBCs, and PLTs, and side-scattered by RBCs, WBCs and PLTs; the method comprises determining at least one of a mean cellular hemoglobin (MCH) and a total hemoglobin (HGB)

concentration by the amount of light absorbed by the RBCs using a single absorbance detector; the method comprises detecting light absorbed by the RBCs in the sample mixture in the flow cell by a single absorption detector; the amount of light absorbed by the RBCs is detected by an absorption detector within a first cone of a first predetermined number of degrees around the incident light; the first predetermined number of degrees is from about 17 to about 26 degrees; the method comprises measuring an amount light side-scattered by the RBCs, WBCs, and PLTs outside the first cone and within a second cone of a second predetermined number of degrees around the incident light; the second predetermined number of degrees around the incident light is from about 75 degrees to about 105 degrees.

According to an additional embodiment of the present invention, a system for measuring concentrations of blood cell components is provided. The system comprises: an optical source configured to emit light at a predetermined wavelength; a flow cell at least partially disposed within the light emitted by the optical source, the flow cell configured to carry a liquid sample mixture through at least a portion of the light emitted by the optical source; a first lens disposed between the optical source and the flow cell; a second lens disposed between the first lens and the flow cell; and a first optical detector configured to detect light emitted by the optical source and absorbed by the sample mixture within a first cone of a first predetermined number of degrees around the incident light.

According to further embodiments: the first predetermined number of degrees is from about 17 to about 26 degrees; the system comprises a second optical detector configured to detect light emitted by the optical source and side-scattered by the sample mixture outside the first cone and within a second cone of a second predetermined number of degrees around the incident light; the second predetermined number of degrees around the incident light is from about 75 degrees to about 105 degrees; the first lens comprises a first predetermined thickness and the second lens comprises a second predetermined thickness, and wherein the first predetermined thickness is less than the second predetermined thickness; the first lens comprises a thickness of about 4.2-6.2 mm and the second lens comprises a thickness of about 4.6-6.6 mm; the first lens is disposed a first predetermined distance from the second lens and the second lens is disposed a second predetermined distance from the flow cell, and wherein the first predetermined distance is greater than the second predetermined distance; the first predetermined distance is at least about two times greater than the second predetermined distance; the first predetermined distance is about 61 mm and the second predetermined distance is about 26 mm; the first lens is disposed a first predetermined distance from the second lens and the second lens is disposed a second predetermined distance from the flow cell, and wherein the first predetermined distance and the second predetermined distance are configured to provide light to the flow cell at about 400 nm to about 450 nm; the first lens and the second lens are disposed between the optical source and the flow cells at respective positions such that the flow cell receives the light from the optical source at about 400 nm to about 450 nm; the first optical detector comprises a single absorbance detector configured to determine at least one of a mean cellular hemoglobin (MCH) and a total hemoglobin (HGB) concentration by the amount of light absorbed by red blood cells (RBCs); the first optical detector is configured to collect light within the first cone in order to measure light absorbed by the red blood cells (RBCs) and light scattered by white blood cells (WBCs) and platelets (PLTs); the system comprises a second optical detector configured to detect light emitted by the optical source and side-scattered by the RBCs, WBCs, and PLTs in the sample mixture outside the first cone; the optical source emits light at a wavelength of 400 nm to 450 nm.

BRIEF DESCRIPTION OF THE DRAWINGS

The above and other aspects, features and advantages of certain embodiments will be more apparent from the following detailed description taken in conjunction with the accompanying drawings, in which:

FIG. 11 is a table of actual and theoretical channel values with and without DC signal baseline restore correction.

FIG. 4A is at a higher 17 degree scatter signal gain than 4B and 4C to show where PLTs appear on the scatterplot.

FIGS. 34, 35 and 36 are tables of Absorption Cross Sections for RBCs ranging from 15 fL/23 g/dL to 300 fL/36.5 g/dL.

FIG. 40 illustrates exemplary parameters for using method and system described herein.

DETAILED DESCRIPTION OF THE PRESENT INVENTION

Figure 1:
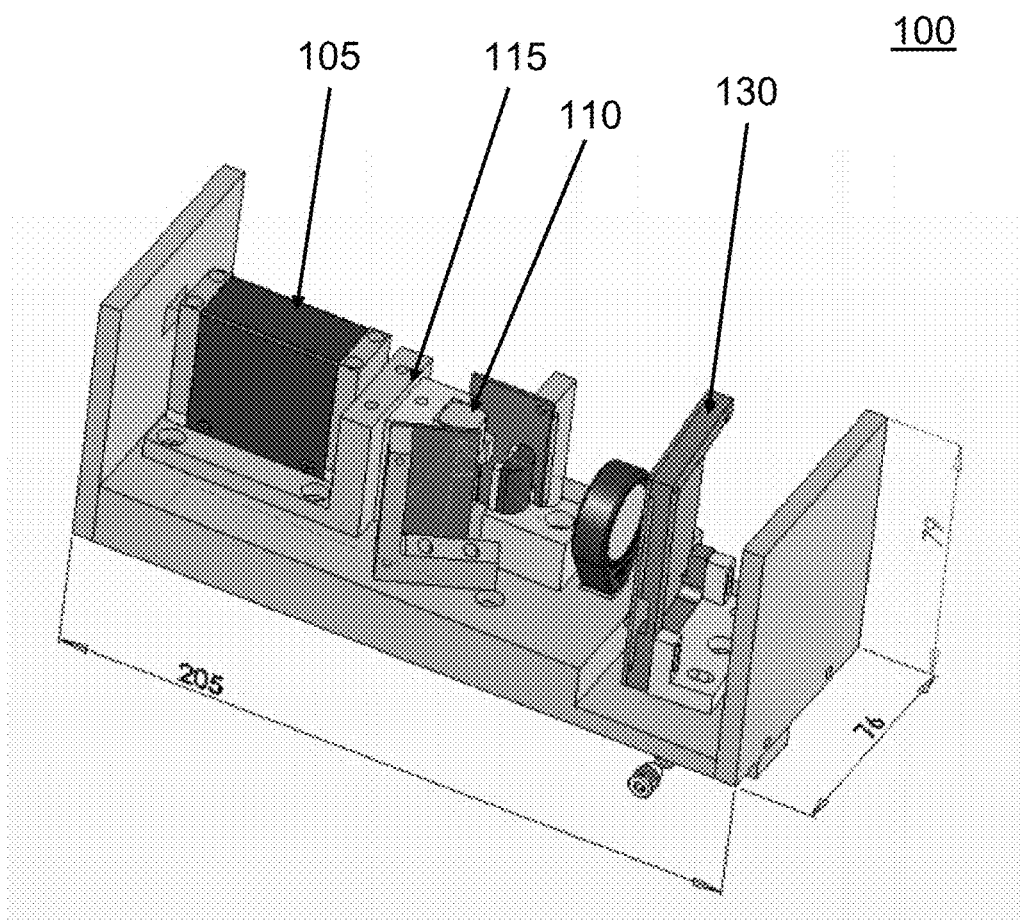
FIG. 1 illustrates a system for measuring concentrations of blood cell components according to an embodiment.

The following detailed description of certain embodiments will be made in reference to the accompanying drawings. In the detailed description, explanation about related functions or constructions known in the art are omitted for the sake of clearness in understanding the concept of the invention, to avoid obscuring the invention with unnecessary detail. Reference to individual embodiments, whether by number of embodiment or relevant feature of the embodiment, is used for convenience in describing such embodiments. Moreover, reference to individual embodiments does not indicate that any of such embodiments are preferred over any other embodiments. Furthermore, each individual embodiment may be combined with any other individual embodiment whether or not expressly stated.

According to embodiments of the present invention, a system and method is provided for distinguishing red blood cells, including nucleated red blood cells, from white blood cells and platelets, including those of humans, avians, reptilians and all other chordates with red blood cells, requiring only one automated flow cytometric analysis cycle, an absorption detector, a side scatter detector, and no red blood cell lysis. It uses 400-450 nm illumination, preferably laser diode illuminated at 403-408 nm or 405-407 nm. The system and method utilize a single reagent. The reagent is comprised of an aqueous solution of salts whose tonicity is between 260-330 milliosmolar, or between 280-300 mOsm, or between 285-295 mOsm. In certain embodiments, $NaNO_2$ is added to the reagent, while maintaining tonicity, to convert oxyhemoglobin in the red blood cells to MetHemoglobin and thus maximize the absorption signal difference between RBC on the one hand, and WBC and PLT on the other, increasing the absorption signal by as much as approximately 20%. In another embodiment, a surfactant is added, while maintaining tonicity, to sphere human and other mammals' red blood cells. The system and method use one detection channel arranged to collect light scatter in a cone of 17 degrees in order to effectively measure only light absorption in red blood cells and another channel to collect light scattered from 75-105 degrees, so-called side scatter. The reagent serves as the blood sample diluent and suspension medium, the flow cytometric sheathing fluid, and the inter-sample rinsing solution. In an embodiment, the reagent contains one or more surfactants to sphere mammalian red blood cells.

According to a further embodiment, a system and method is provided for determining mean cellular hemoglobin content (MCH pg), and overall hemoglobin concentration (HGB, g/dL) in mammalian, avian, reptilian, or any chordate whole blood sample containing red blood cells using a single measurement cycle involving the measurement of light absorption and right angle scatter only.

According to a further embodiment, a system and method are provided for distinguishing RBC, including NRBC, from WBC and PLT for human, non-human mammalian, avian, reptilian, and other chordate blood samples and for determining MCH and HGB, requiring only a single optical source at 400-450 nm, or 400-440 nm, or 403-408 nm, or 405-407 nm, a single optical flow cell, a single reagent, an optical detector to collect light scattered within a 17 degree cone around light beam incidence and another to collect light scatter from 75-105 degrees.

As further described herein, embodiments of the present invention provide a system and method for distinguishing blood components. In particular embodiments the system and method described herein distinguish RBC, including nucleated red blood cells (NRBC), from WBC and PLT. In certain embodiments, the system and method described herein distinguishes RBC and NRBC from WBC and in a single flow cytometric analysis cycle using a single reagent, an absorption detector and a right angle scatter detector. The system and method also provides for determination of mean cellular hemoglobin content (MCH) and overall hemoglobin concentration (HGB). The single reagent serves as sample diluent, flow cytometric sheath, and inter-sample rinse. The single reagent includes water-soluble salts such as NaCl, and may also include $NaNO_2$ and one or more surfactants.

In conjunction with one or more further additional detectors a white blood cell differential (Diff) analysis can be performed all with the single reagent in a single measurement cycle. The analysis cycle time is less than or equal to 60 seconds including sample aspiration, dilution and suspension, flow cytometric analysis and inter-sample channel rinsing. This provides a sample throughput of greater than 60 samples per hour, equaling the output of current blood component measuring systems. The system and method may be applied to the complete blood count/white blood cell (CBC/Diff) analysis of avians, reptilians and all chordates with red blood cells as well as of humans and other mammals.

There are currently no methods to measure absorption of hemoglobin by single RBCs directly using flow cytometry and no methods using this measurement for distinguishing between RBC on the one hand and WBC and PLT on the other. Further, no methods exist for the determination of mean cellular hemoglobin MCH (pg) or overall hemoglobin concentration (HGB (g/dL)) using a single absorption detector to measure individual cell hemoglobin content. Furthermore, no methods exist for distinguishing nucleated red blood cells (NRBC) from WBC in the same measurement cycle as for RBC and PLT. Finally, no method exists that achieves the above and other advantages using a single reagent that contains only water soluble salts. Also, no automated method exists for discriminating among the RBC, WBC, and PLT of non-mammalian chordate whole blood samples. Also no automated exists that distinguishes between RBC and PLT over the entire physiologic range encountered in humans.

Accordingly, the above and other advantages and improvements are provided herein by the embodiments of the system and method for distinguishing RBC, including nucleated red blood cells (NRBC), from WBC and PLT. The cytometric flow optical system is configured to operate according to the methods described herein. Furthermore, the methods described herein utilize the cytometric flow optical system for distinguishing RBC, including NRBC, from WBC and PLT for human, non-human mammalian, and other chordate blood samples and for determining MCH and HGB. The embodiments described with respect to the cytometric flow optical system utilize the methods described herein and the methods described herein operate utilizing the cytometric flow optical system whether or not expressly stated. Each of the embodiments of the system can be combined with each of the embodiments of the method in any combination.

An advantage of the system and method described herein is that RBCs and NRBCs can be distinguished on the one hand and PLTs and WBCs on the other using only a single absorption detector. In certain embodiments, RBCs and NRBCs can be distinguished and PLTs and WBCs can be distinguished by collecting incident light within a 21 degree cone to 26 degree cone. Thus, using the system and method described herein a single channel, instead of two or more channels, can gate RBCs so that other channels can be used to determine the concentration of WBC cell types including neutrophils, lymphocytes, monocytes, eosinophils, and basophils.

Figure 5:
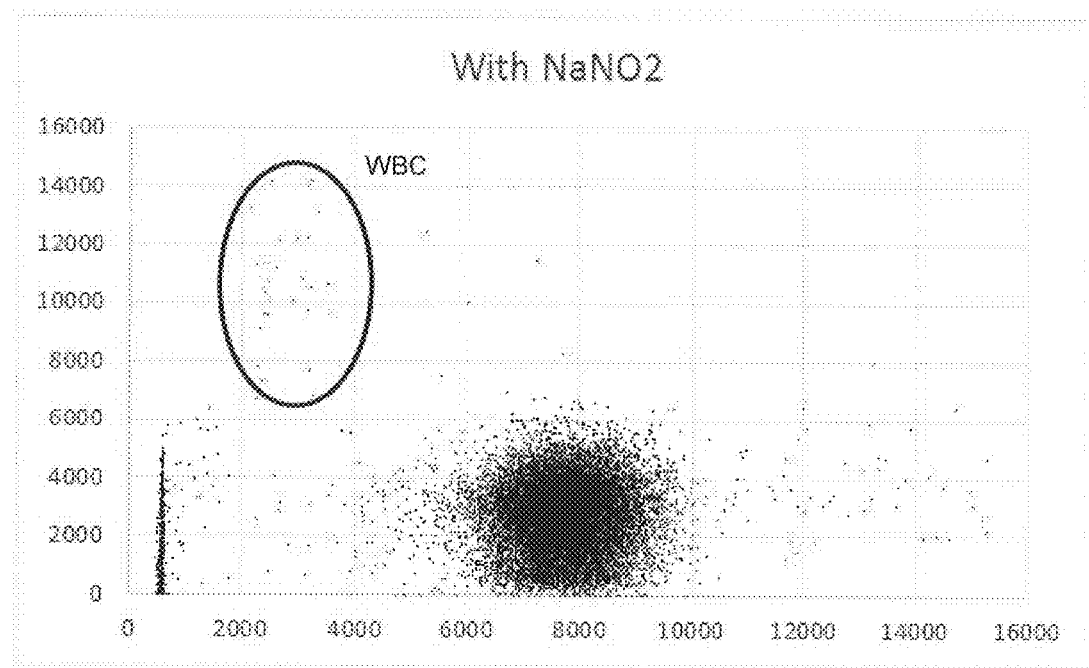
FIGS. 5 and 6 are side scatter vs. absorption scatterplots for whole blood samples drawn from the same collection tube and diluted 1000-fold into a media with surfactant and $NaNO_2$ and in a medium with surfactant but no $NaNO_2$, respectively.
Figure 6:
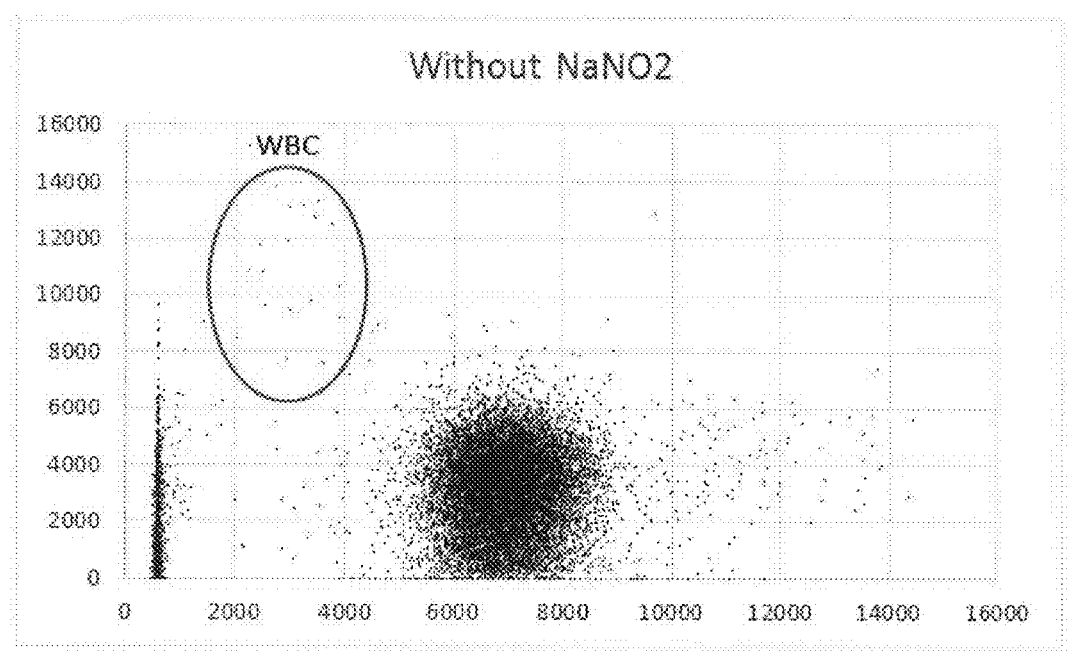

A method for measuring concentrations of blood cell components includes obtaining a blood sample from a subject. In certain embodiments, various other body fluid samples may be utilized in the method including bronchial alveolar lavage, cerebrospinal fluid, synovial fluid and bone marrow. The blood sample may include any combination of red blood cells (RBCs), white blood cells (WBCs), and platelets (PLTs). The blood sample is mixed with a non-lysing aqueous solution to form a sample mixture. The non-lysing aqueous solution may include a reagent that converts oxyhemoglobin to methemoglobin present in the sample mixture while substantially maintaining the tonicity in a range of about 260-330 milliosmolar (mOsm). The reagent that converts oxyhemoglobin to methemoglobin may be $NaNO_2$ or other suitable reagent, such as other nitrite salts. The sample mixture may also include at least one surfactant to sphere the RBCs. In certain embodiments, the surfactant Brij 35 or sodium dodecyl sulfate. The reagent includes an aqueous solution of salts whose tonicity is between 260-330 milliosmolar (mOsm), in certain embodiments between 280-300 mOsm, and in certain embodiments between 285-295 mOsm. In certain embodiments, $NaNO_2$ is added to the reagent, while maintaining tonicity, to convert oxyhemoglobin in the blood sample to MetHemoglobin. The addition of $NaNO_2$ maximizes the absorption signal difference between RBC and WBC and PLTs, increasing the absorption signal difference by as much as 20%, as is apparent from FIGS. 5 and 6. In FIGS. 5 and 6, the absorption signal for the RBCs in $NaNO_2$ is more than 10% higher than in the other medium, while the WBC signal position, indicated by the encircled region labeled "WBC," on the absorption axis is unaffected. Note that the absorption signal described here is measured as a direct drop in transmission and not as the negative log of the transmission. The hemoglobin in RBC absorbs light intensely in the Soret band, e.g., 400-450 nm. The peak wavelength depends on the ligation of the heme groups. For MetHemoglobin (MetHgb), the peak is at approximately 406 nm. Also, at 406 nm MetHgb absorption intensity coefficient is approximately 75% greater than that of oxyhemoglobin, the predominant form encountered by automated instrumentation. The difference in absorption signal at 406 nm is only about 20% because the signal represents a transmission loss, not its logarithmic transform.

In certain embodiments, the reagent does not include fluorescent dyes. In certain embodiments, the reagent does not include monoclonal antibodies. Such reagents are not needed in the system and method described herein.

The method includes injecting the sample mixture as a suspension a flow cell. The sample mixture is passed through the flow cell and light is emitted towards the flow cell. An amount of light absorbed by the RBCs is measured by a detector and an amount of light scattered by WBCs, and PLTs is measured by the detector. A concentration of each of the RBCs, WBCs, and PLTs present in the sample mixture is determined from the measured amount of light absorbed by the RBCs and scattered by the WBCs and PLTs. It is noted that the amount of light absorbed by the RBCs is measured concurrently with the amount of light scattered by the WBCs. Furthermore, the RBCs are present in the sample mixture when the amount of light scattered by the WBCs is measured. The system and method described herein enables measurement of RBCs, PLTs, and WBCs in a single analysis step, which reduces the cost of reagents to run the system and method, and reduces the number of components such as separate reaction chambers, separate syringes, and separate transmission lines.

In certain embodiments, the method includes detecting light absorbed by the RBCs in the sample mixture in the flow cell by a single absorption detector. The amount of light absorbed by the RBCs is detected by the detector within a cone around the incident light from about 17 to about 26 degrees. That is, the detector accepts light in a cone around the forward direction that includes 0-17 degrees in every direction or up to 0-26 degrees in every direction. While not being bound by a particular theory, it is believed that 0-21 degrees includes more than 97% of light scattered by any of the cell types. The cone can be increased to capture up to 0-26 degrees in every direction to ensure that little or no scattered light is lost. It is believed that less than 1% of incident light is scattered by RBC, PLT, WBC outside a 26 degree cone.

The method includes determining mean cellular hemoglobin (MCH) concentration and a total hemoglobin (HGB) concentration present in the sample mixture by the amount of light absorbed by the RBCs using a single absorption detector. Accordingly, the system and method described herein enables determination of HGB concentration and MCH concentration using a single detector, in a manner that requires less hardware and fewer reagents than other methods, particularly for certain species, such as chordates.

In certain embodiments, a second detector is used to detect side-scattered light. Using the second detector, the method includes measuring an amount of light side-scattered by the RBCs, WBCs, and PLTs and distinguishing between the concentrations of RBCs, WBCs and PLTs from the amount of light absorbed by the RBCs, the amount of light scattered by the WBCs, and PLTs, and the amount of light side-scattered by the RBCs, WBCs, and PLTs. Using the amount of measured light side-scattered by the RBCs, WBCs, and PLTs, overlap between the amount of light absorbed by the RBCs and the amount of light scattered by the WBCs, and PLTs from the amount of light side-scattered by the RBCs, WBCs, and PLTs is resolved in order to determine the concentration of each of the RBCs, WBCs, and PLTs. The method comprises measuring an amount light side-scattered by the RBCs, WBCs, and PLTs outside the first cone and within a second cone around the incident light from about 75 degrees to about 105 degrees.

According to the methods described herein, scattering and absorption are determined. In the current context, absorption is distinguished from extinction. Extinction refers to total light lost by the incident light beam from the forward direction and is the sum of light lost due to scatter and light lost due to absorption. Scattering refers to light re-directed by the particle from the forward direction. It is commonly reported as an overall scattering "cross-section" as well as scattering intensity vs. scattering angle. The angle spectrum signature is particle specific and is used to determine the detector scheme for the flow cytometer. Absorption refers to light lost due to absorption, which is not angle-dependent and uses a dedicated absorption detector. A single value is reported as the absorption "cross-section".

In certain embodiments, the subject is a mammal, such as a human. Where the subject is a human, the blood sample includes human red blood cells (HRBCs), human white blood cells (HWBCs), and human platelets (HPLTs), and the method further includes distinguishing between the HRBCs and the HPLTs across a human physiologic range of RBC sizes and PLT sizes. The human physiologic range of RBC sizes includes about 15 fL to about 180 fL and a human physiologic range of PLT sizes of about 1 fL to about 60 fL. The method includes distinguishing between the HRBCs and the HPLTs across a human physiologic range of component concentrations of about 1000/microliter to about 1,500,000/microliter of PLTs and of about 250,000/microliter to about 7,000,000/microliter of RBCs.

In certain embodiments, the blood sample includes nucleated red blood cells (NRBCs). The method is not subject to NRBC interference with WBC/Diff unlike standard automated methodologies. The large nuclei of NRBCs can be present in the lymphocyte size range, so that measurements depending on size are affected. NRBCs are not present in significant quantities in normal human blood, with the exception of normal newborns and in regenerative anemias associated with hemolysis or blood loss. The NRBCs produced in the bone marrow, but not normally released into circulation before they mature and extrude the nuclei, are needed by the organism to replenish abnormally diminished peripheral supplies. However, in chordates, all RBCs are nucleated and the system and method described herein can be utilized to distinguish and measure the blood components of chordate blood samples. The method includes measuring an amount of light absorbed by the NRBCs and determining a concentration of the NRBCs present in the sample mixture from the measured amount of light absorbed by the NRBCs and scattered by the WBCs and PLTs.

The above-described method is utilized on the system described below. FIG. 1 illustrates a system 100 for measuring concentrations of blood cell components according to an embodiment. The system 100 includes an optical source 105. The optical source 105 is configured to emit light at a range of wavelengths that may be adjusted according to requirements of a sample being analyzed, including from about 400 nm to about 450 nm, in certain embodiments about 400 nm to about 420 nm, in certain embodiments about 403 to about 408 nm, and in certain embodiments about 405 to about 407 nm. The optical source may be embodied as, for example, a laser diode, or other suitable light source.

The system 100 further includes a flow cell 110 at least partially disposed within the light emitted by the optical source 105. The flow cell 110 is configured to carry a liquid sample mixture through at least a portion of the light emitted by the optical source 105. The optical flow cell 110 is configured to provide the sample as a liquid stream, i.e., a concentric stream of suspended cells within a sheath stream sheath fluid, through the light path of the optical source 105. The liquid stream carries the sample that is to be analyzed.

Figure 2:
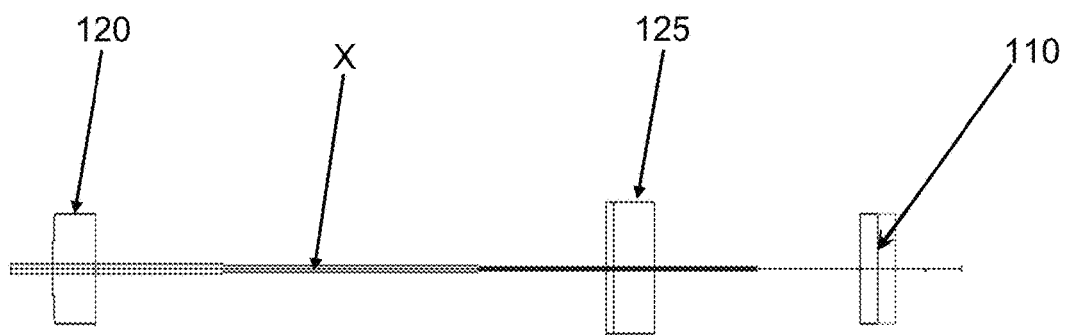
FIG. 2 illustrates the internal configuration of a lens housing.

The system 100 includes a lens housing 115. FIG. 2 illustrates the internal configuration of the lens housing 115. FIG. 2 illustrates the light X emitted from the optical source 105. The lens housing 115 includes a first lens 120 disposed between the optical source 105 and the flow cell 110. The lens housing 115 includes a second lens 125 disposed between the first lens 120 and the flow cell 110. The first lens 120 has a thickness of about 4.2-6.2 mm, and in certain embodiments, about 5.2 mm. The second lens 125 a thickness of about 4.6-6.6 mm, and certain embodiments, about 5.6 mm. The first lens 120 is disposed a distance of about 56.5 mm to about 66.5 mm, or about 61 mm from the second lens 125. The second lens 125 is disposed a distance of about 24.2 to about 28.2 mm, or about 26 mm from the flow cell 110. The distance between the first lens 120 and the second lens 125 and the distance between the second lens 125 and the flow cell 110 are configured to provide light X to the flow cell 110 at about 400 nm to about 450 nm. In other words, the first lens 120 and the second lens 125 are disposed between the optical source 105 and the flow cell 110 at respective positions such that the flow cell 110 receives the light X from the optical source 105 at about 400 nm to about 450 nm.

The system 100 includes a first optical detector 130 configured to detect light emitted by the optical source 105 and absorbed by the sample mixture. The first optical detector 130 detects light within a first cone around the incident light of about 17 to about 26 degrees. In certain embodiments, the first optical detector 130 is a single absorbance detector, reducing cost and reduced system complexity. In certain embodiments, the first optical detector 130 uses a single detection channel configured to collect light scattered in a cone of plus or minus 23 degrees in order to measure only light absorption of the RBCs. The first optical detector 130 is configured to determine at least one of a mean cellular hemoglobin (MCH) and a total hemoglobin (HGB) concentration by the amount of light absorbed by red blood cells (RBCs). The first optical detector 130 is configured to collect light within the first cone in order to measure light absorbed by the red blood cells (RBCs) and light scattered by white blood cells (WBCs) and platelets (PLTs).

Figure 3:
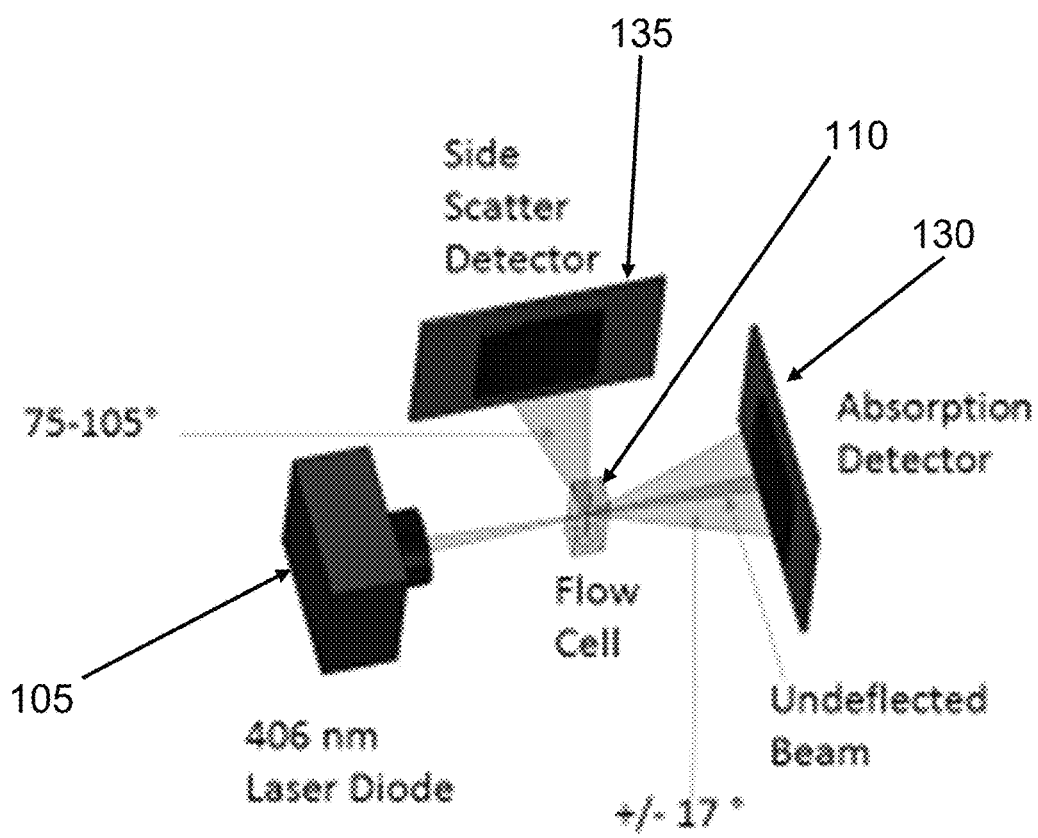
FIG. 3 illustrates the system including a second optical detector, according to alternative embodiment.

FIG. 3 illustrates the system 100 including a second optical detector 135, according to alternative embodiment. The second optical detector 135 is configured to detect light emitted by the optical source 105 and side-scattered by the RBCs, WBCs, and PLTs in the sample mixture outside the first cone. The second optical detector 135 is configured to detect light emitted by the optical source 105 and side-scattered by the sample mixture outside the first cone and within a second cone around the incident light from about 75 degrees to about 105 degrees. It is noted that the system 100 and method described herein can be configured to operate using only the first optical detector 130 for measuring concentrations of blood cell components.

The system 100 further includes a computer processor (not shown) configured to control the operation of each of the components therein. The processor is configured to process information received from the optical detector. The computer processor is also configured to adjust various parameters of the cytometric flow system. In certain embodiments, the computer processor may output information received from the optical detector to a computer for further processing. The computer processor is configured to run software and/or firmware that performs the functions and methods described herein.

Examples

Figure 4:
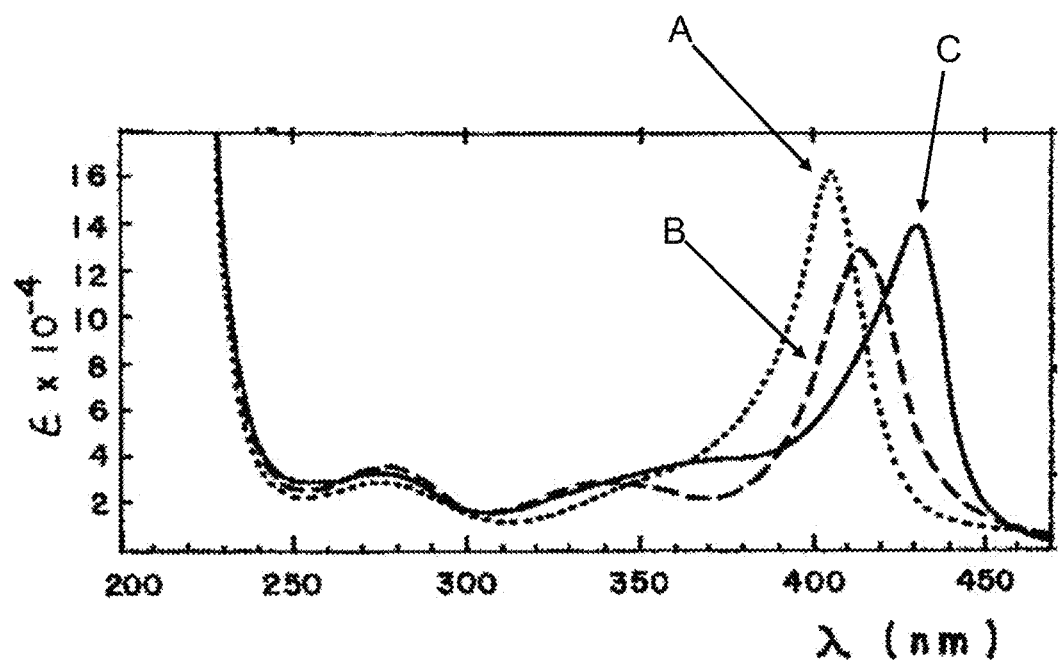
FIG. 4 illustrates absorption spectra in the Soret band for (A) MetHGB; (B) OxyHGB; and (C) HGB.

FIG. 4 illustrates absorption spectra in the Soret band for (A) MetHGB; (B) OxyHGB; and (C) HGB. Note shifts of peak position and relative absorption intensities. Also, note that epsilon (extinction coefficient) is for each of four heme subunits, so that total epsilon is four times the value shown.

FIGS. 5 and 6 are side scatter vs. absorption scatterplots for whole blood samples drawn from the same collection tube and diluted 1000-fold into a medium with surfactant and $NaNO_2$ and in a medium with surfactant but no $NaNO_2$, respectively.

Figure 7A:
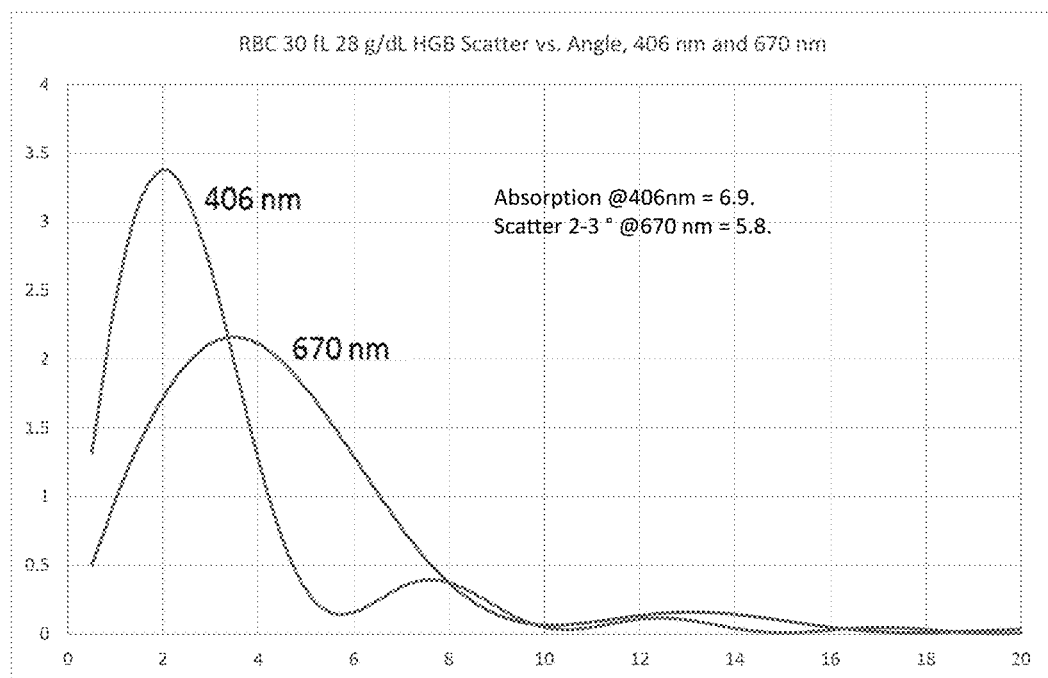
FIGS. 7A, 7B, and 7C illustrate the 0-20 degree scatter and absorption for RBC signals of 30 fL volume/28 g/dL MCHC, 60 fL volume/28 g/dL MCHC, and 90 fL volume/34 g/dL MCHC respectively, at 406 nm and 670 nm based on Mie scattering theory.

FIG. 7A illustrates scatter and absorption signals for 30 fL, 28 g/dL RBC at (a) 406 nm; and (b) 670 nm based on Mie scattering theory. A wavelength of 670 nm is commonly used in conventional cytometric flow instruments. One conventional cytometric flow instruments measures scatter between 2 and 3 degrees. The scattering signal is 5.8 arbitrary units, compared to the absorption signal for these cells, which is 6.9 arbitrary units.

Figure 7B:
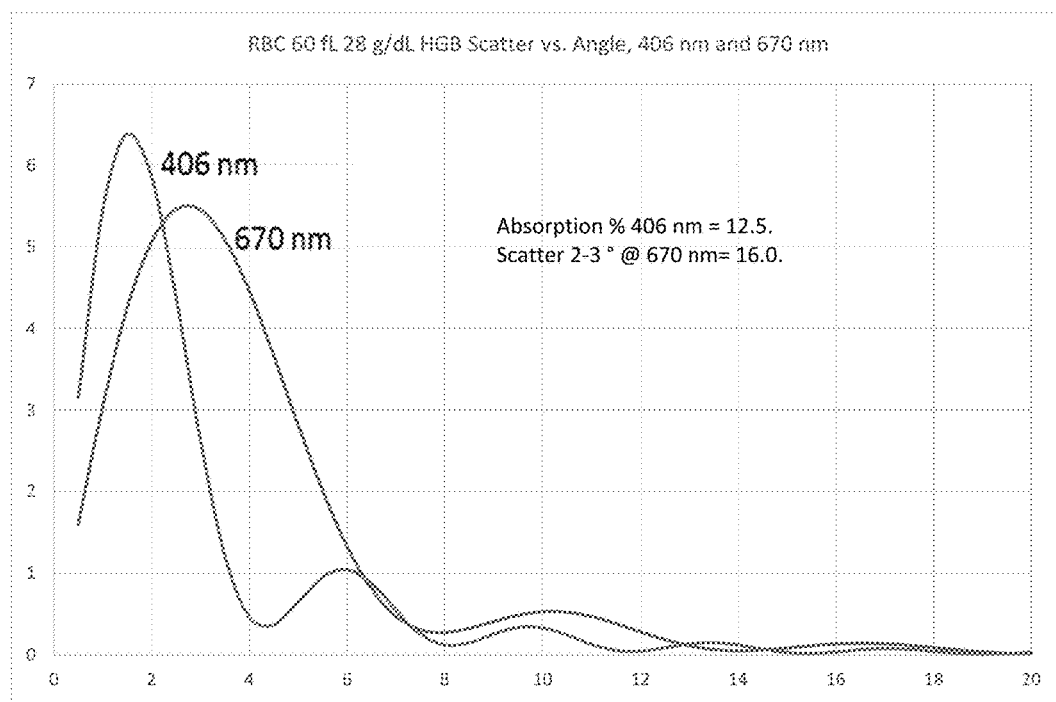

FIG. 7B illustrates scatter and absorption signals for 60 fL, 28 g/dL RBC at: (a) 406 nm; (b) and 670 nm. The 2-3 degree scattering signal of 16 arbitrary units, compared to 12.5 arbitrary units for absorption.

Figure 7C:
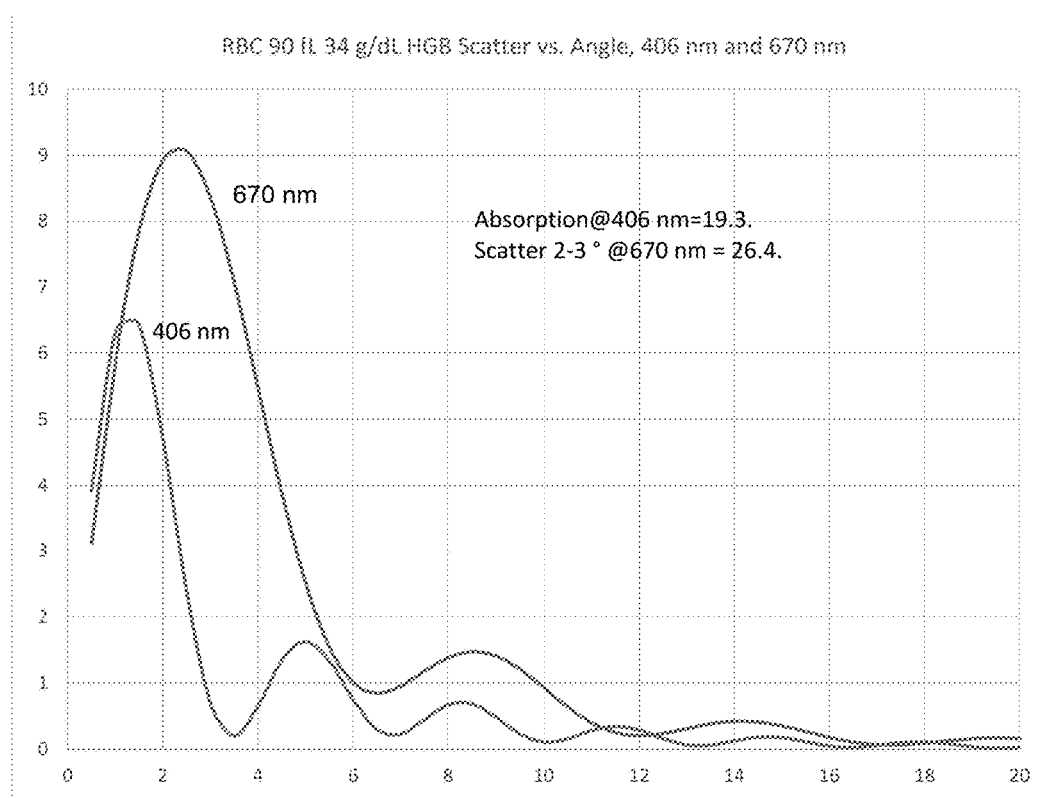

FIG. 7C illustrates scatter for signals for 90 fL, 34 g/dL RBC at: (a) 406 nm; (b) and 670 nm. The 2-3 degree scattering is 26.4 arbitrary units compared to 19.3 units obtained for absorption. Based on the relative values over the range of RBC volumes and hemoglobin concentrations, the signal strengths for the method disclosed herein are comparable to those known by one of ordinary skill in the art.

A minimum of two analysis cycles are required for conventional flow cytometric instruments because of the absolute and relative concentrations of RBC and WBC in normal human whole blood. The RBC count range is 3.5 million-5.5 million/microliter, WBC count range is 4,000-12,000/microliter so that the RBC/WBC ratio range is 300-800, typically approximately 700. Therefore, to count at least 3,500 WBC in whole blood to achieve adequate WBC/Diff precision, 2.45 million RBC must be counted. This processing speed can be achieved, e.g. 50,000 cells/second for approximately 50 seconds. However, at this counting rate in optical flow cytometers, the counting event coincidence rate is typically 4%-8%.

Coincidences result in the approximate doubling of scatter signal sizes. RBC scattering signal intensities are smaller than those for WBC and larger than those for most PLTs, and thereby provide discrimination among these cell types. However, the RBC coincidence signals overlap many of the WBC signals. With coincidence of 4-8% of the RBC event count, the coincidence signals obscure some of the WBC signals, which particular ones depend on the scatter detection angle ranges used. Consequently, it is preferred to either reduce the sampling rate to the point where the coincidence rate is negligible, which is impractical commercially because it would require 10 minute or longer cycles per sample and a relatively large volume of sample diluent, or to count and analyze WBC in a separate cycle that requires the elimination of RBC via lysis. The latter approach is taken.

Furthermore, no automated method exists, optical flow cytometric or otherwise, for the determination of RBC, WBC, and PLT counts for avian, reptilian, or other non-mammalian chordate blood samples. Non-mammalian chordate red blood cells are nucleated ovalocytes. The nuclei render the RBC lysis method ineffective because even with lysis, the coincidences owing to RBC nuclei obscure the WBC signals. The coincidence levels in WBC analyses are even greater than in RBC/PLT analyses because the sample dilution factors are much lower in WBC analyses owing to the WBC/RBC ratio. Also, the accuracy of hemoglobinometry, which uses optical absorption, is compromised by the turbidity caused by the large number of nuclei in the hemoglobin solution. The turbidity falsely elevates HGB reported values in chordates with NRBC by 25% or more, even when compensated for turbidity using a 2-wavelength method such as Hemocue™.

Figure 8:
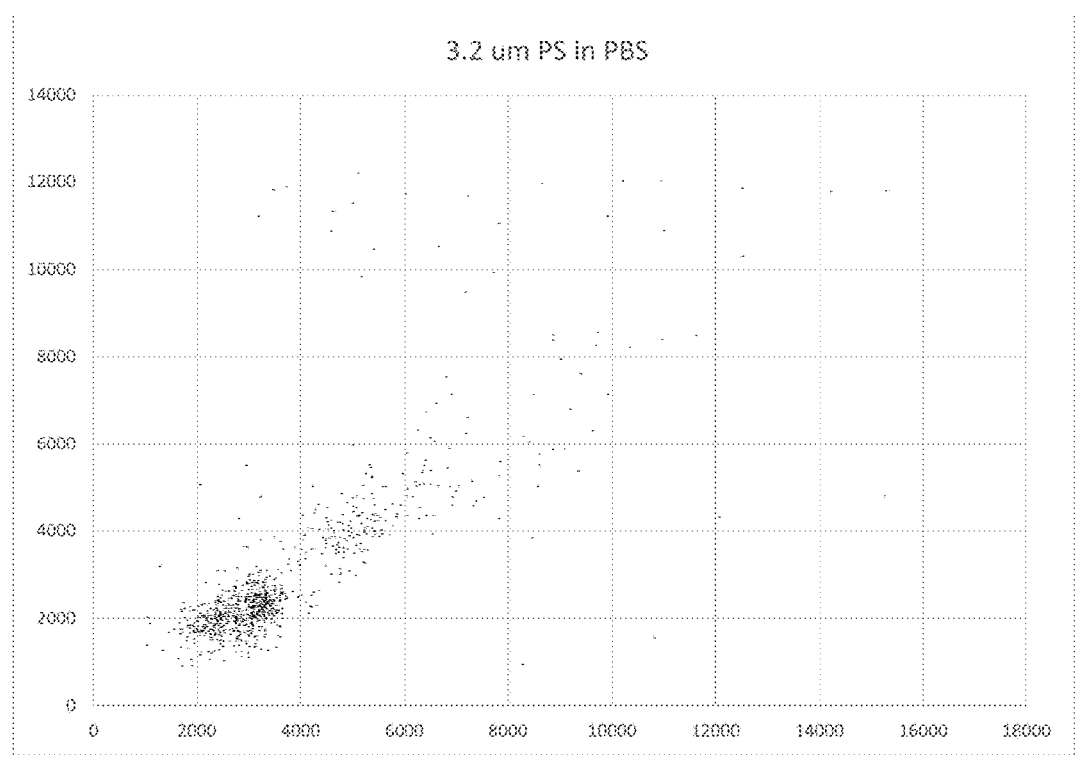
FIGS. 8, 9, and 10 are side scatter vs. 17 degree scatter plots for polystyrene beads of 3.2, 5.0, and 7.0 micron diameter beads.
Figure 9:
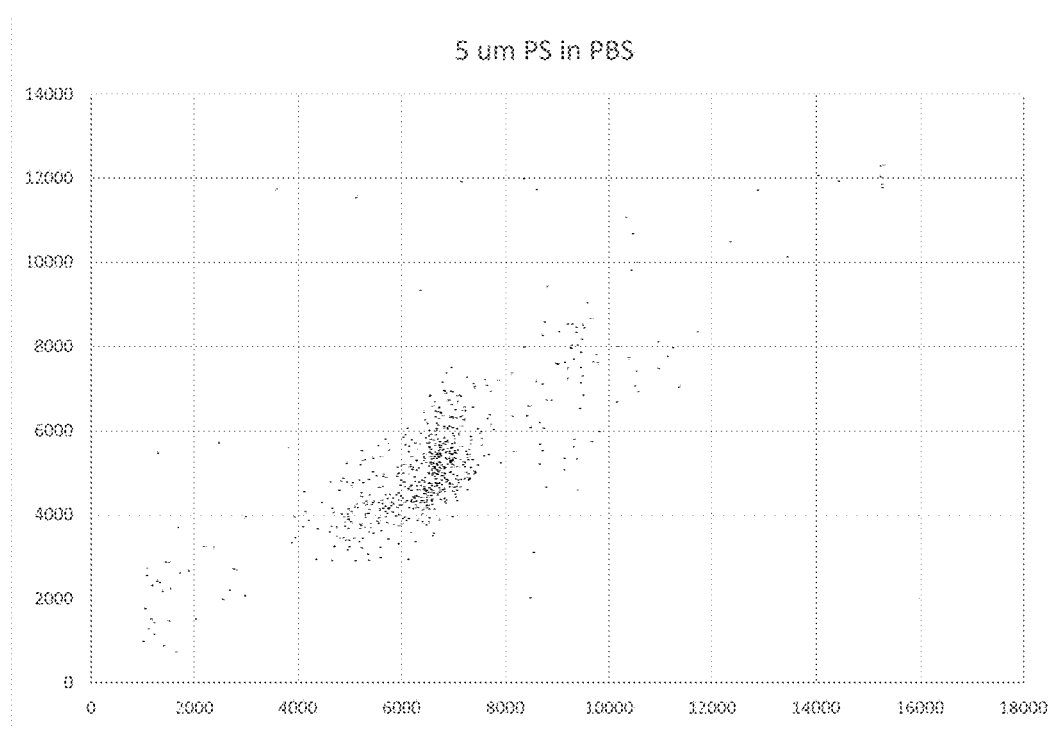
Figure 10:
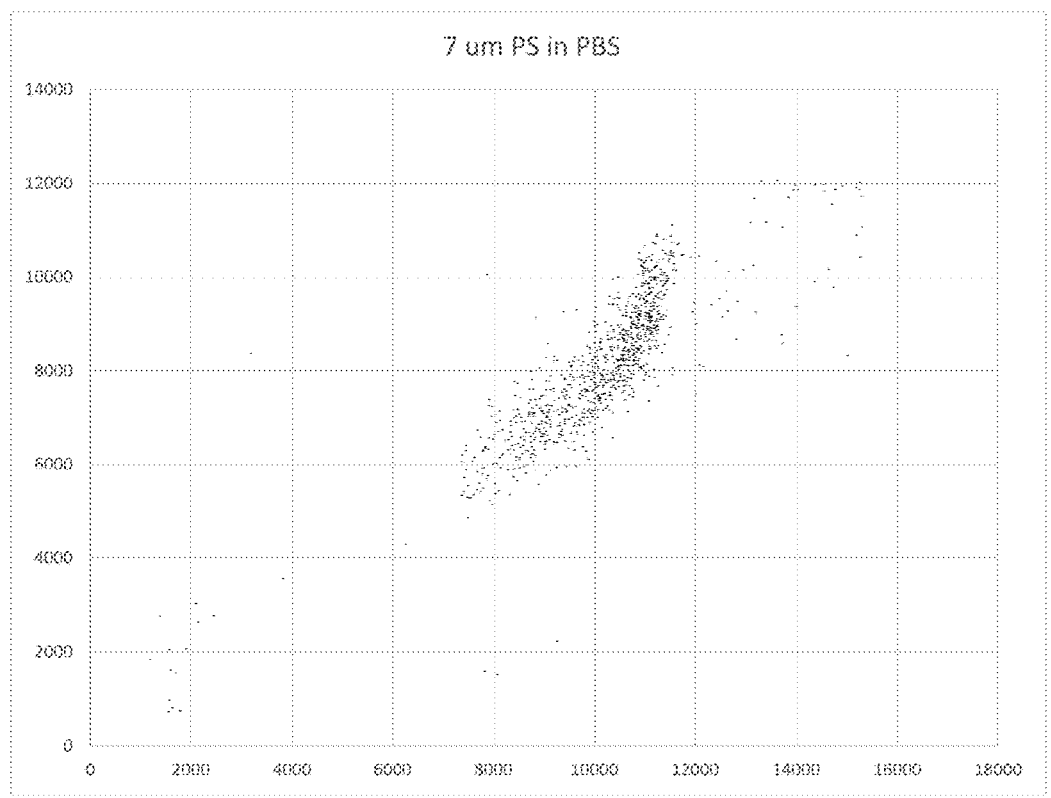

The hemoglobin in RBC absorbs light intensely in the Soret band, e.g., 400-450 nm. The peak wavelength depends on the ligation of the heme groups. As stated above, Mie scattering theory predicts that RBC absorption signals are sufficiently large for counting RBC. FIGS. 8-10 are right-angle scatter vs. 17 degree cone scatterplots for polystyrene beads of 3.2, 5.0, and 7.0 micron beads. Mie theory predicts that owing to their relatively high real refractive index at 406 nm; 1.6262 and non-negligible imaginary refractive index of 0.0003 which relates to light absorption, these particles should scatter significant amounts of light outside 17 degrees as well as absorb some light.

FIGS. 8, 9, and 10 are side scatter vs. 17 degree scatter plots for polystyrene beads of 3.2, 5.0, and 7.0 micron diameter beads.

FIG. 11 is a table of actual and theoretical channel values with and without DC signal baseline restore correction. FIG. 11 is a table of computed signal intensities showing that the signal sizes bracket the range of predicted RBC signals. The ratios of uncorrected polystyrene bead signal size are somewhat skewed. This is because the signals are biased upwards due to DC baseline restore limitations of the optical system. When corrected for this bias, the ratios obtained in practice agree well with predictions. Applying this correction to typical RBC absorption signal means of about 8000, yields means of about 6800, which corresponds to absorption cross sections of about 18.1 as compared to theoretical values of 19.3 based on hematology analyzer MCV, MCHC, and MCH values.

Figure 12:
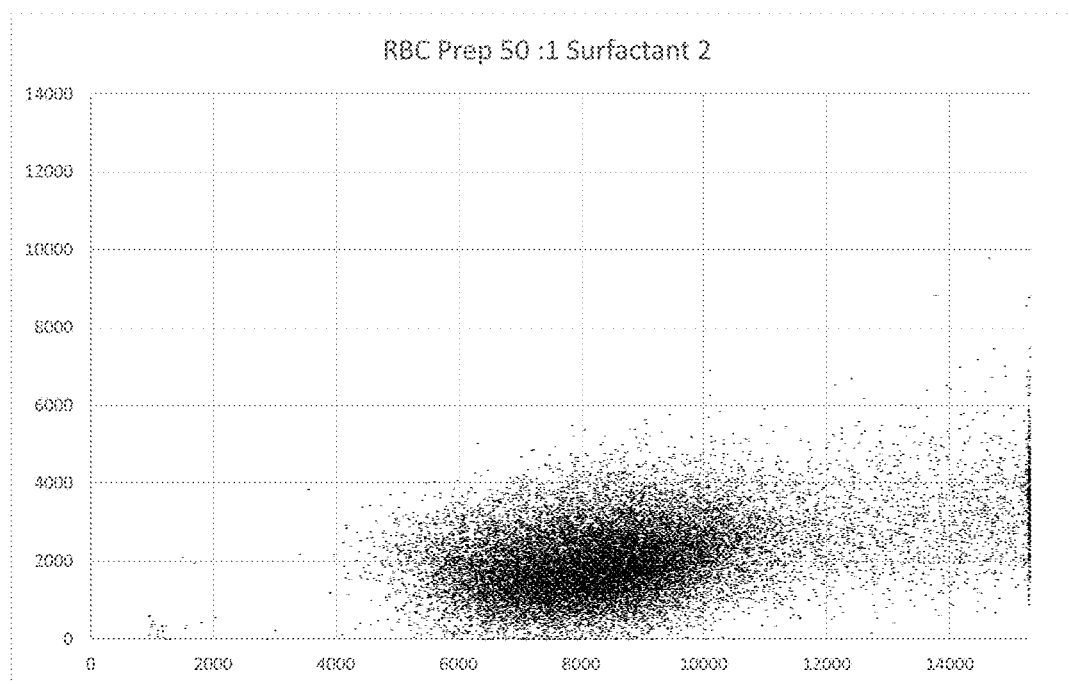
FIGS. 12, 13 and 14 are scatter plots of human RBC preparations that are free of WBCs, in different diluents.
Figure 13:
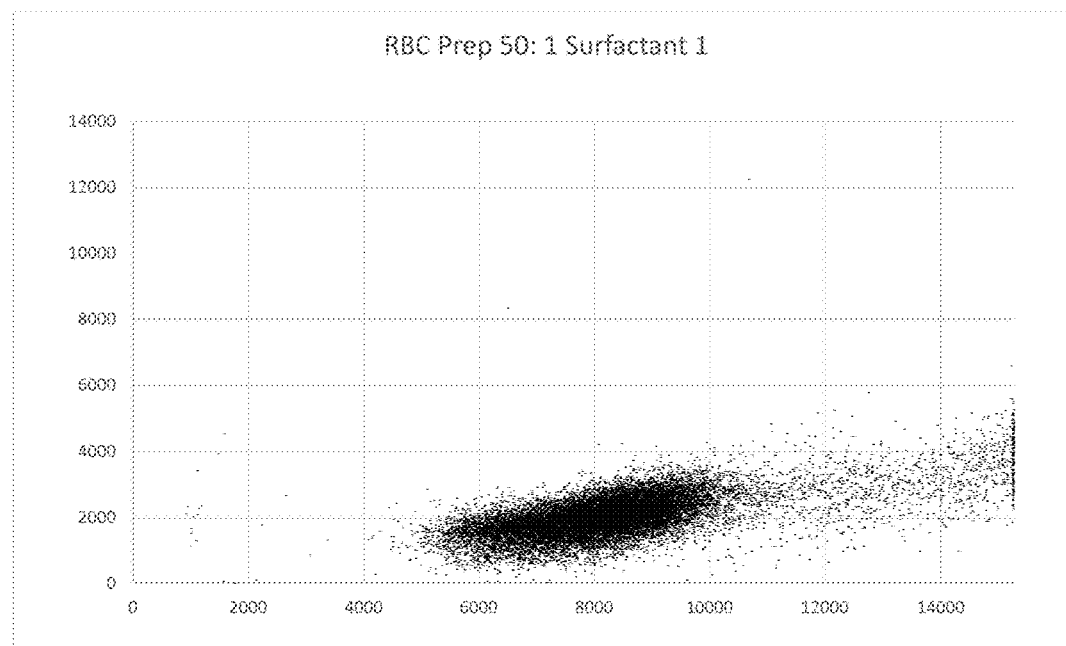

FIGS. 12 and 13 are graphs illustrating that the absorption signal sizes for sphered RBCs are within 10% of the predicted values, when corrected for baseline restore offset.

Figure 14:
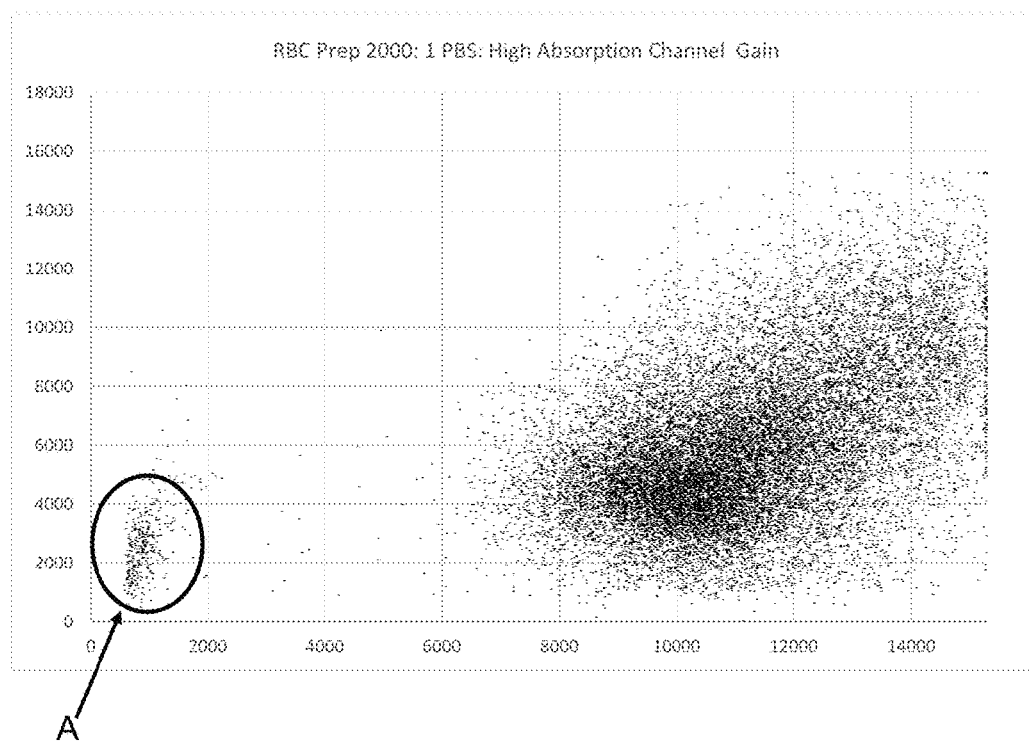

FIG. 14 is a scatterplot of a WBC-free blood sample preparation at high 17 degree cone scatter gain. FIG. 14 illustrates PLT signals within the circle labeled "A." FIGS. 12 and 13, as well FIGS. 19-30 show that at lower channel gains PLT signals are below detection threshold. This demonstrates the gap between RBC and PLT signals. This is as predicted by Mie scattering theory, given the usual size range and real refractive index range of human PLT; 5-12 fL and 1.36-1.385, respectively, and zero imaginary part of the refractive index. FIG. 32 shows that even under conditions of very microcytic and hypochromic RBC; 15 fL/23 g/dL along with very large PLT of normal-high real refractive index, 60 fL/1.38, RBC absorption is more than 4 times as large as PLT scatter signal; 3.21 vs. 0.75 arbitrary units.

Figure 15:
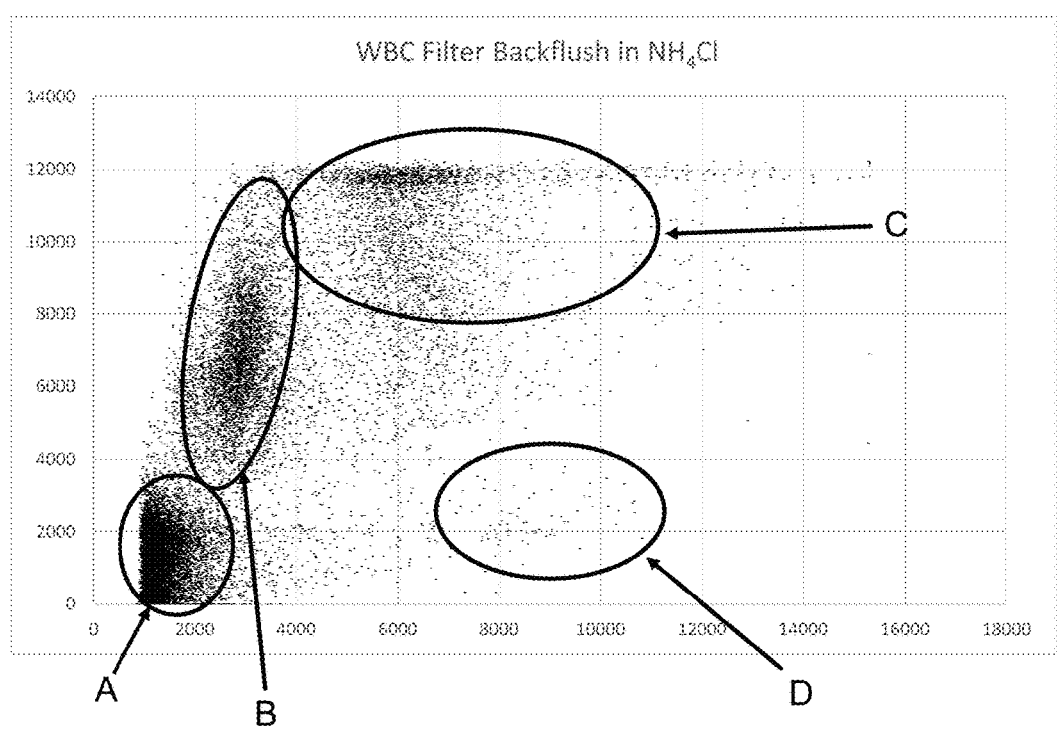
FIG. 15 is a scatterplot of the WBCs and PLTs removed from whole blood during the RBC purification process.

FIGS. 12, 13, and 14 are scatterplots of whole blood samples from which WBC has been removed using Pall Acrodisc™ WBC filters. Note that the scatterplots 12 and 13 contain one cell population corresponding to RBC, and 14 two populations, RBC and some PLT. The upper portions of the scatterplots are empty. This is where the WBC appear, as seen in FIG. 15. FIG. 15 is a WBC+PLT preparation obtained by back-flushing the filter with 0.83% $NH_4Cl$ to capture the WBC and PLT while at the same time gently lysing the residual RBC. FIG. 15 illustrates: (A) PLT coincidences and RBC ghosts; (B) lymphocytes, monocytes and basophils; (C) neutrophils and eosinophils; and (D) residual RBCs. The lower left portion of the scatterplot contains PLT coincidences and RBC ghost signals. RBC "ghost signals" refer to RBCs whose membranes have been violated so that hemoglobin leaks out. Under a microscope the RBCs appear faint, i.e., ghost-like.

Figure 16:
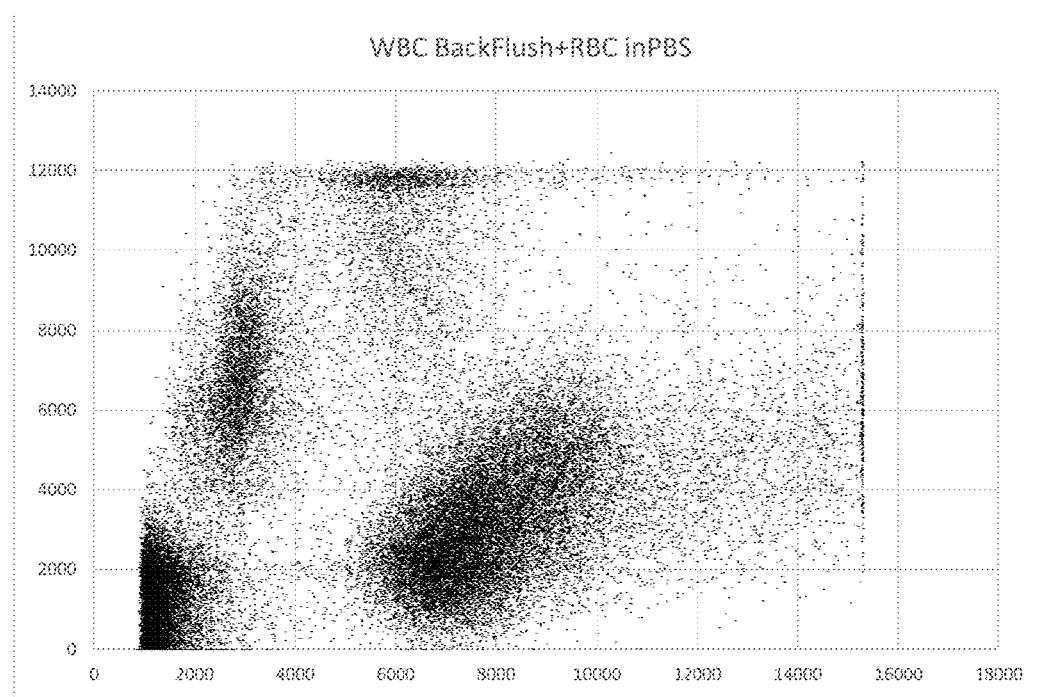
FIGS. 16, 17 and 18 are scatterplots of overlays of RBC preparations in various media and a WBC preparation to show that RBCs, PLTs, and WBCs are distinct.
Figure 17:
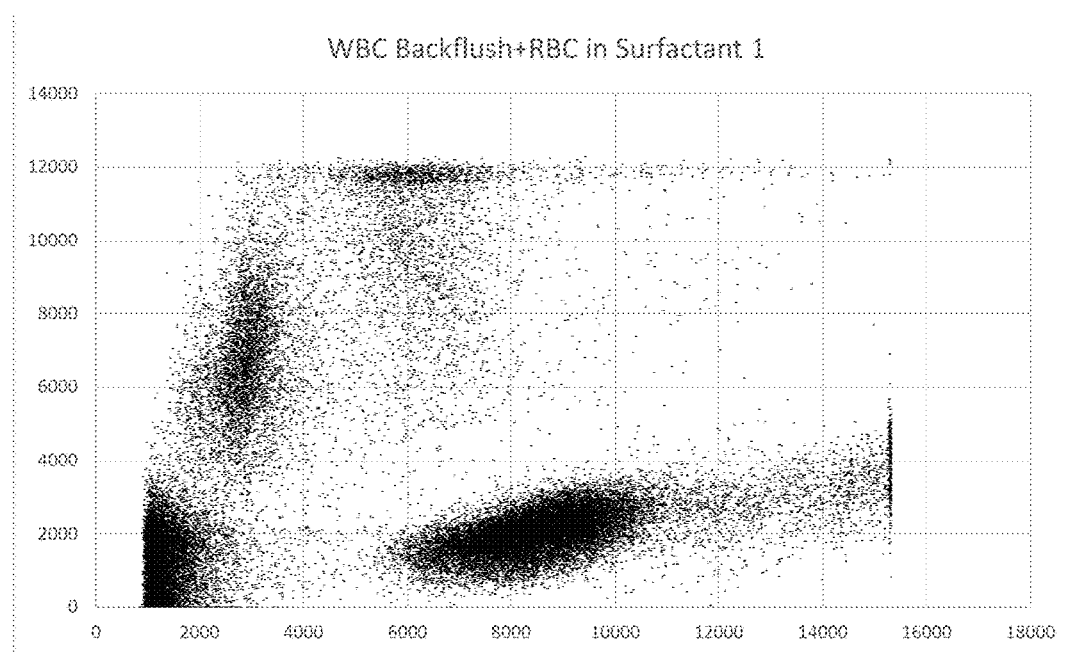
Figure 18:
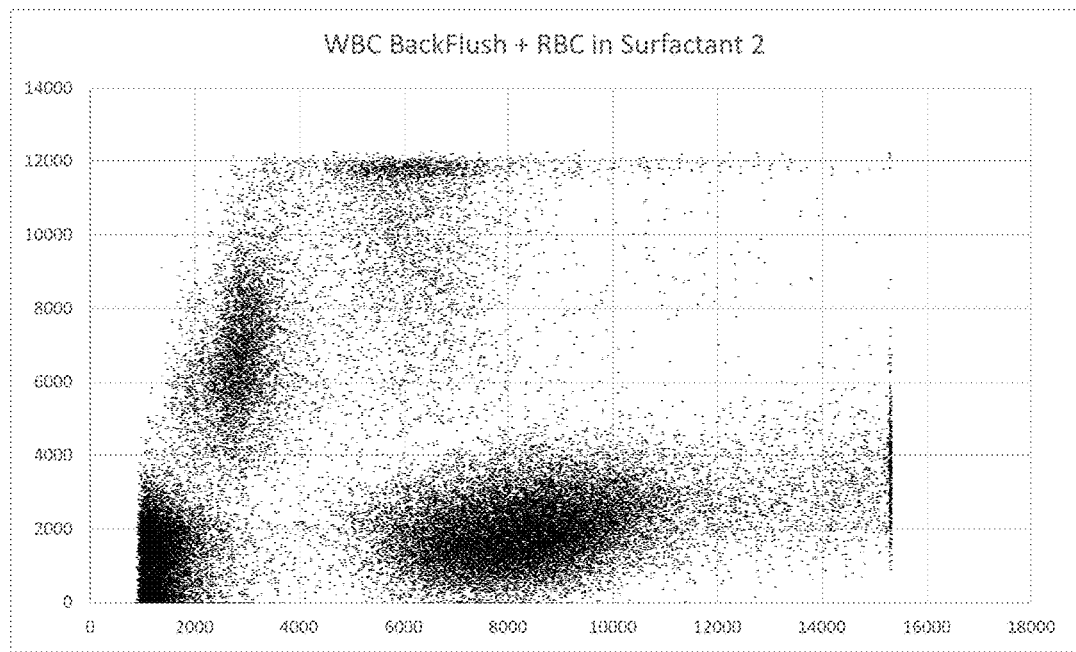
Figure 19:
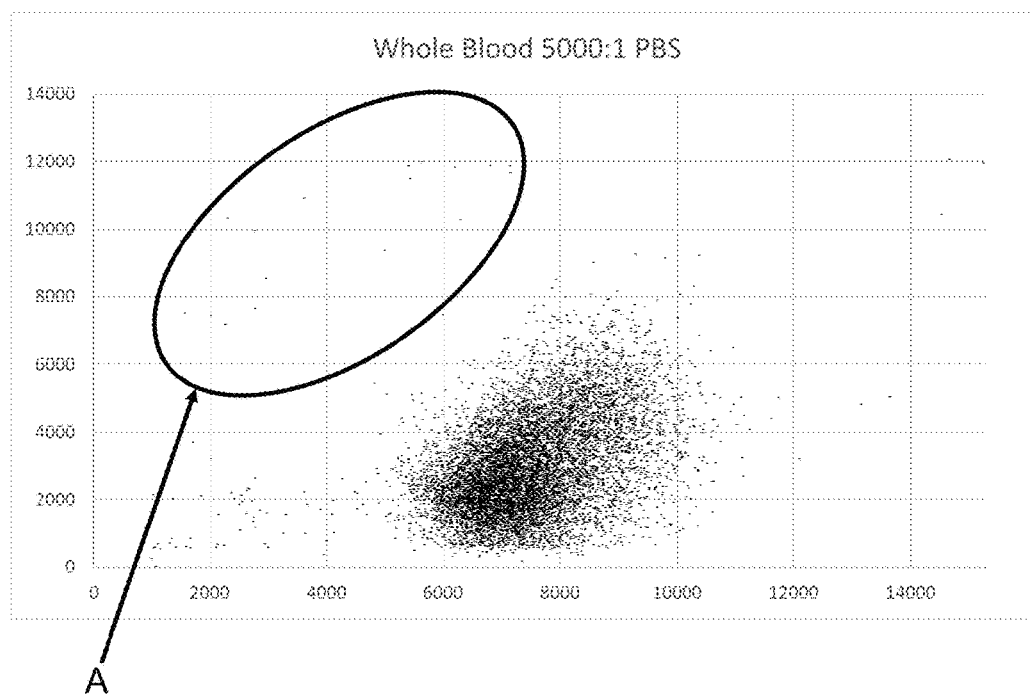
FIG. 19-30 are scatterplots of whole blood samples suspended into various media at 5000:1, 500:1, and 50-1 dilution to show that high RBC coincidence rates do not cause RBC-WBC signal overlap.
Figure 20:
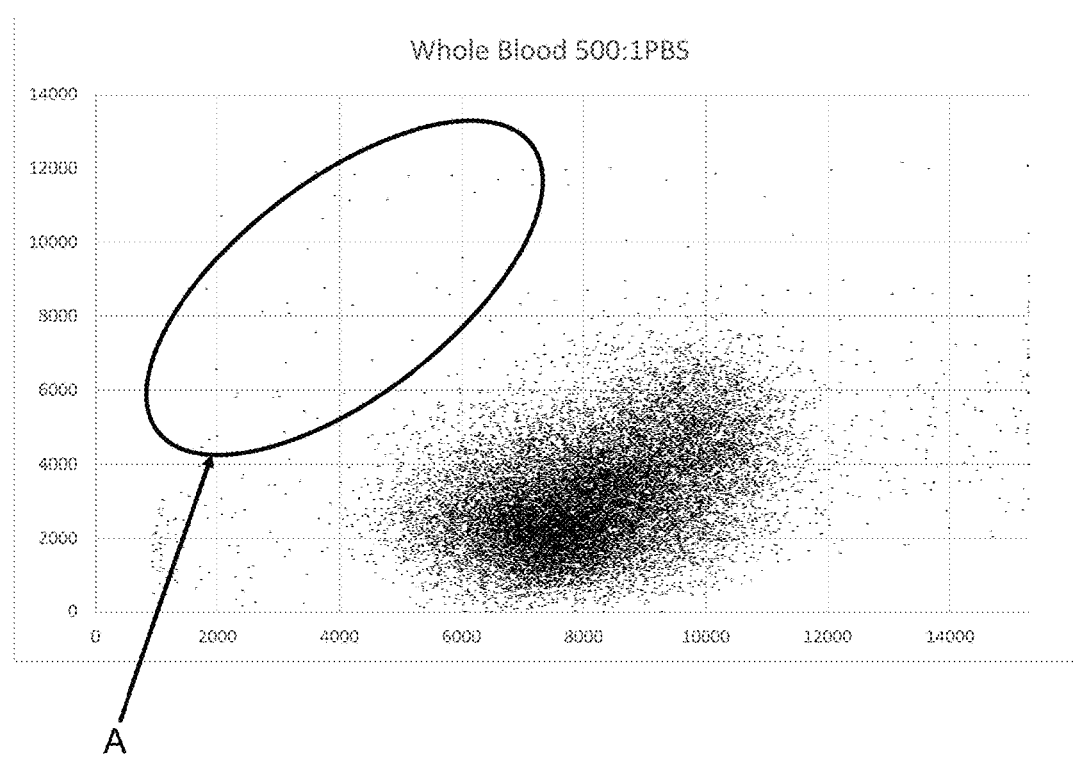
Figure 21:
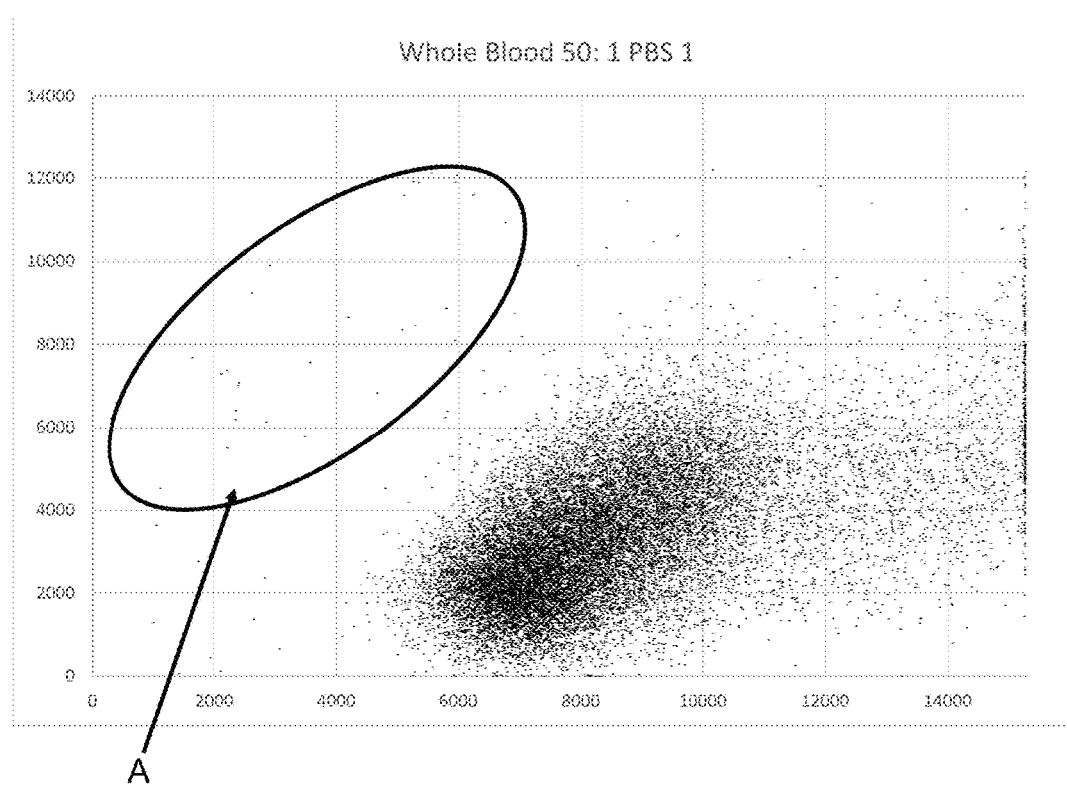
Figure 22:
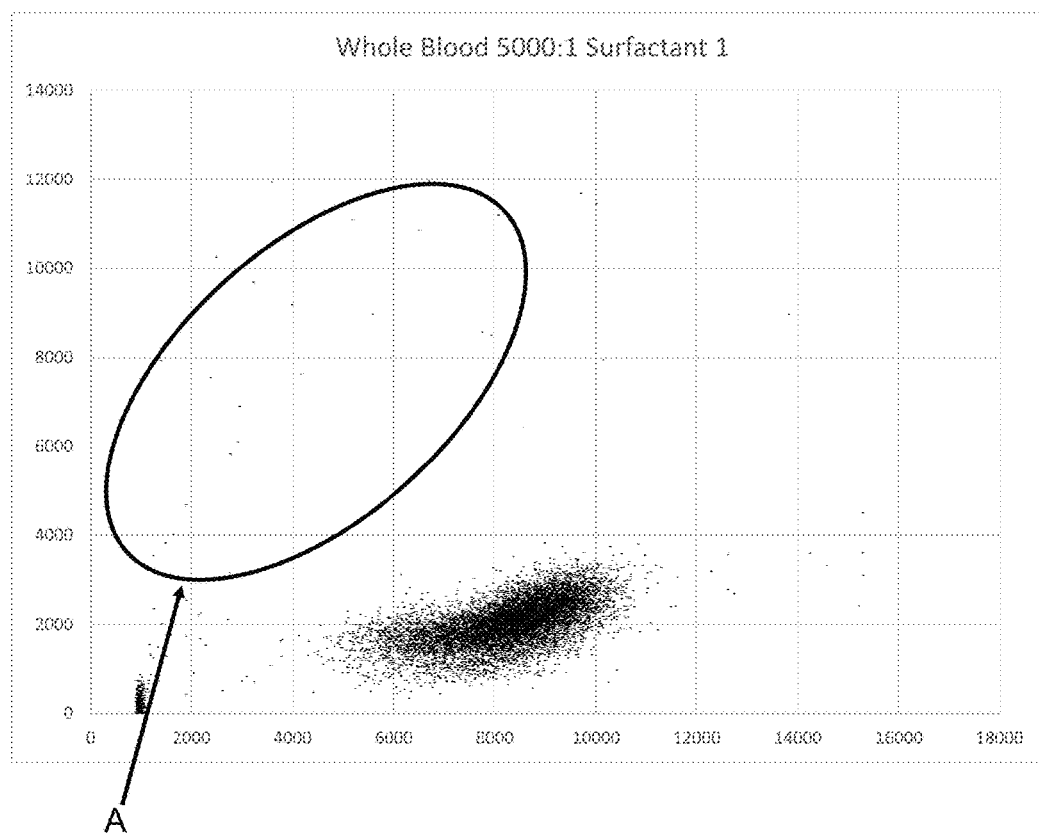
Figure 23:
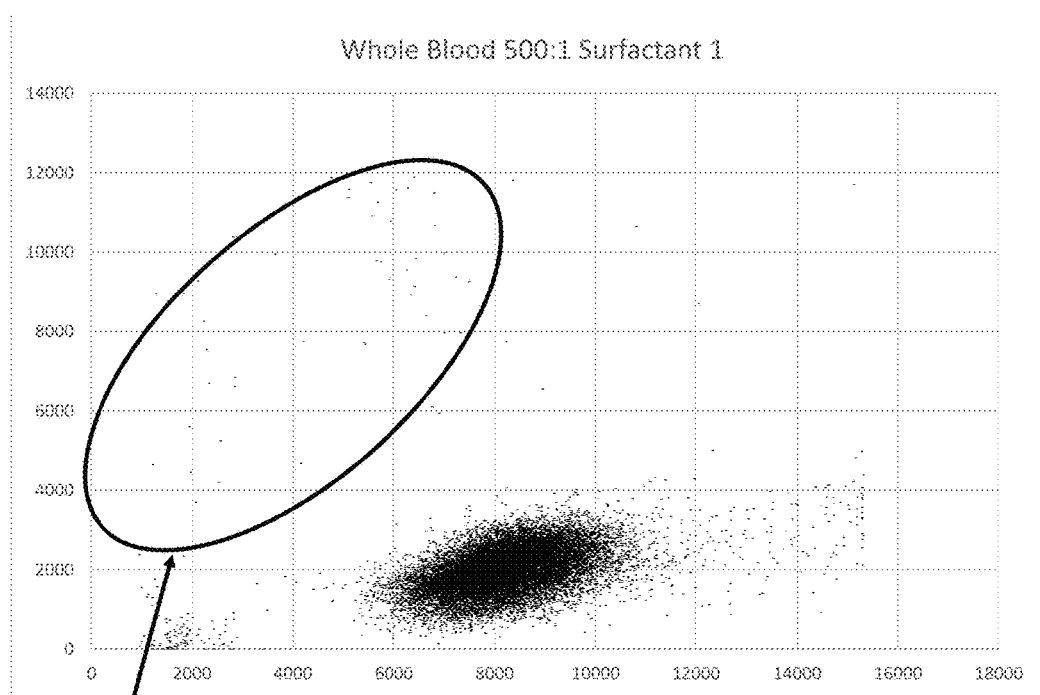
Figure 24:
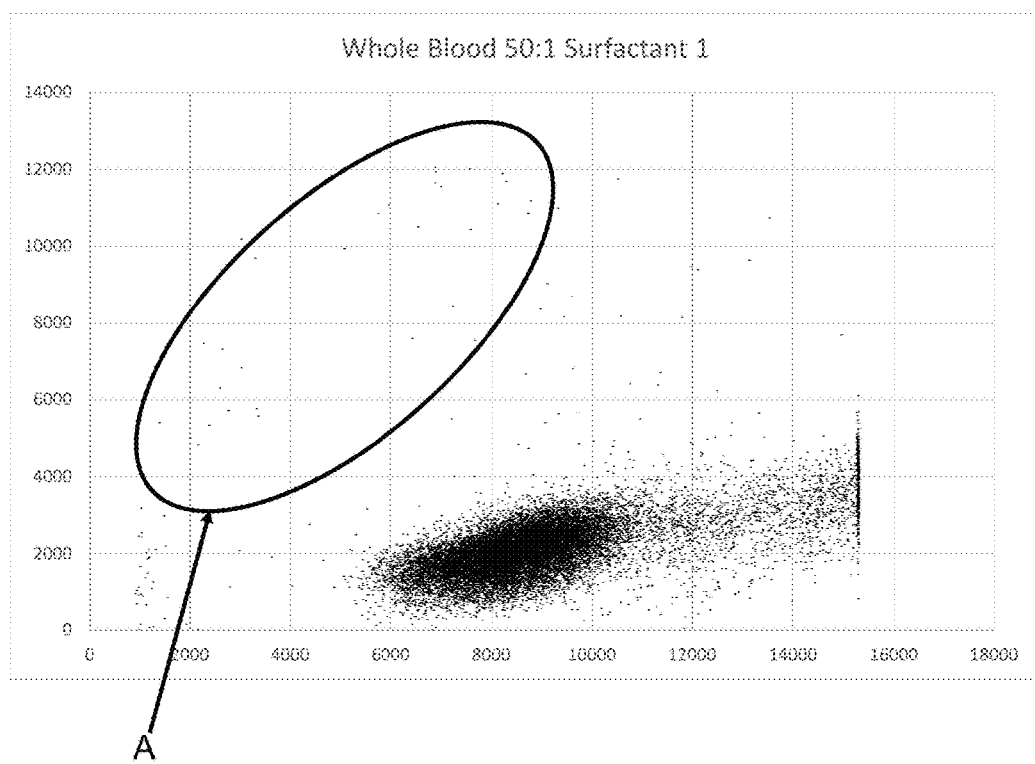
Figure 25:
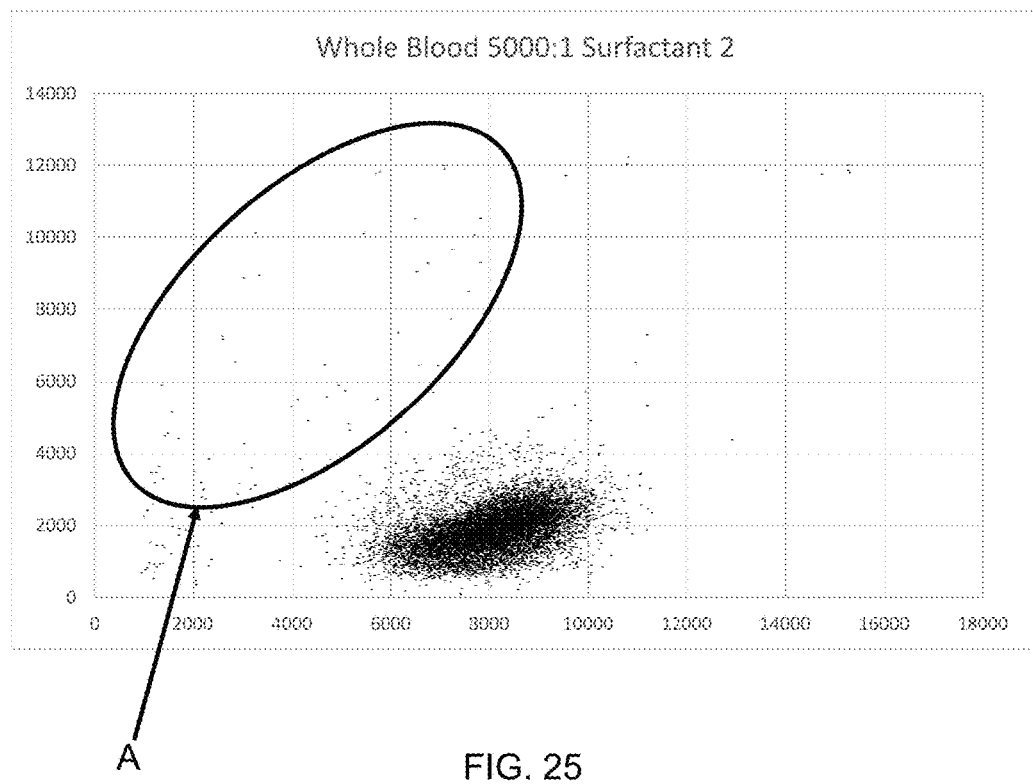
Figure 26:
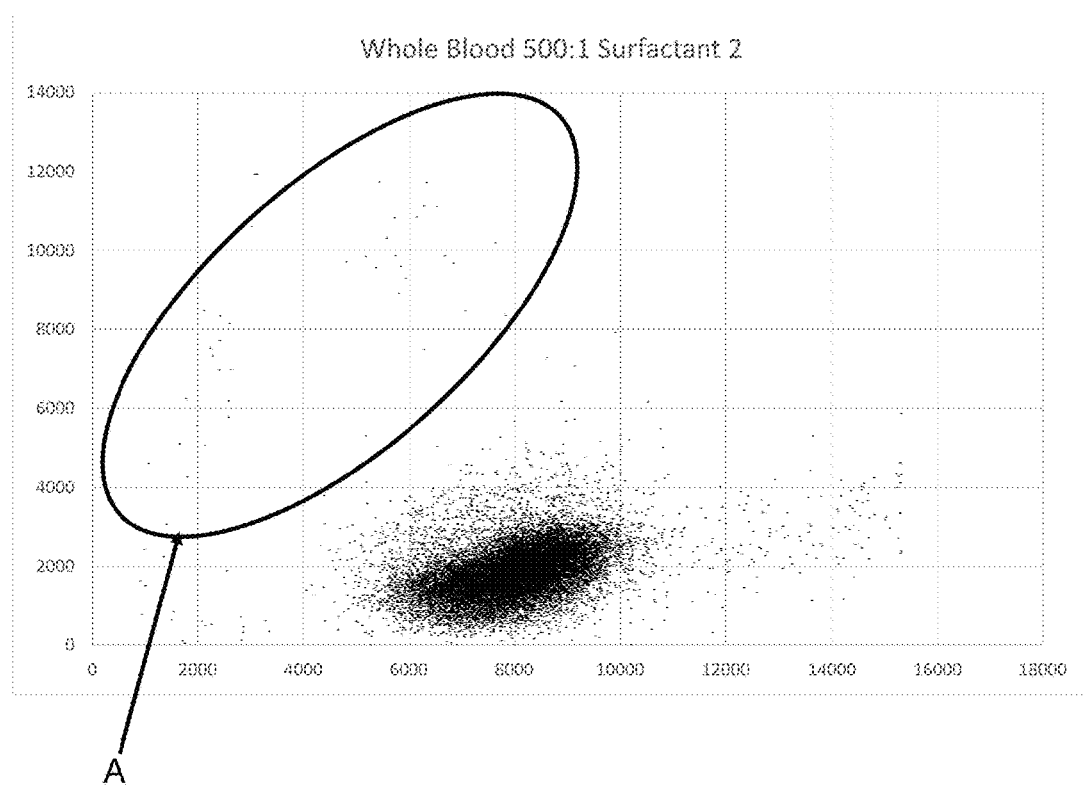
Figure 27:
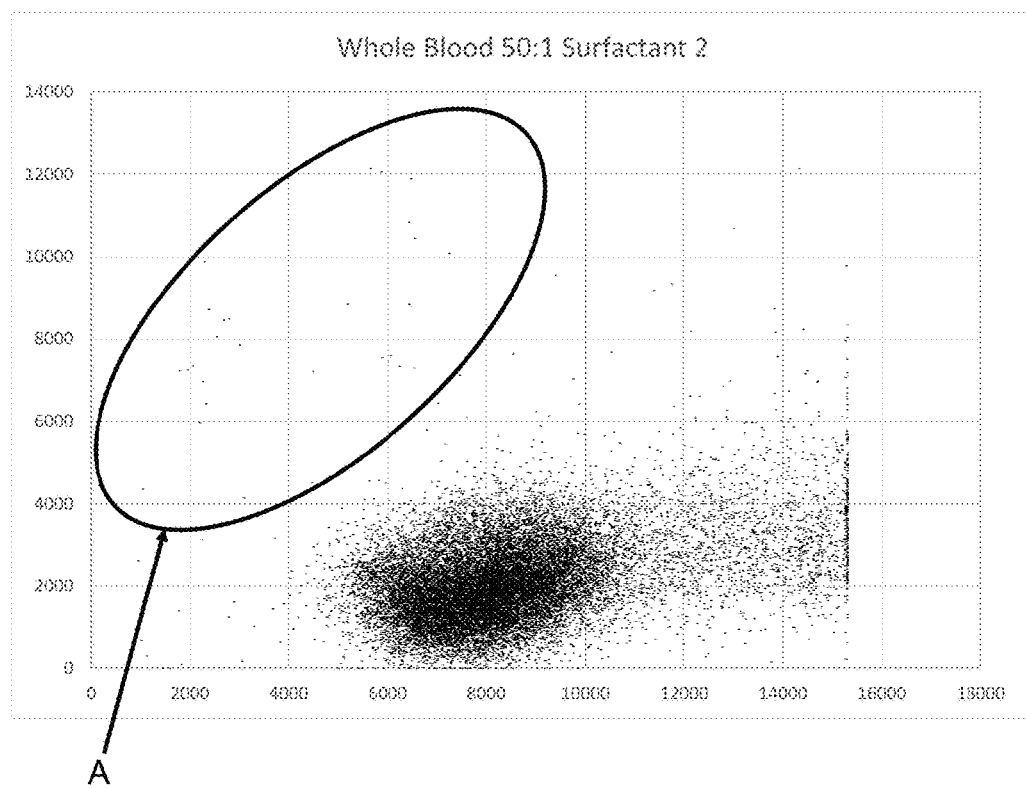
Figure 28:
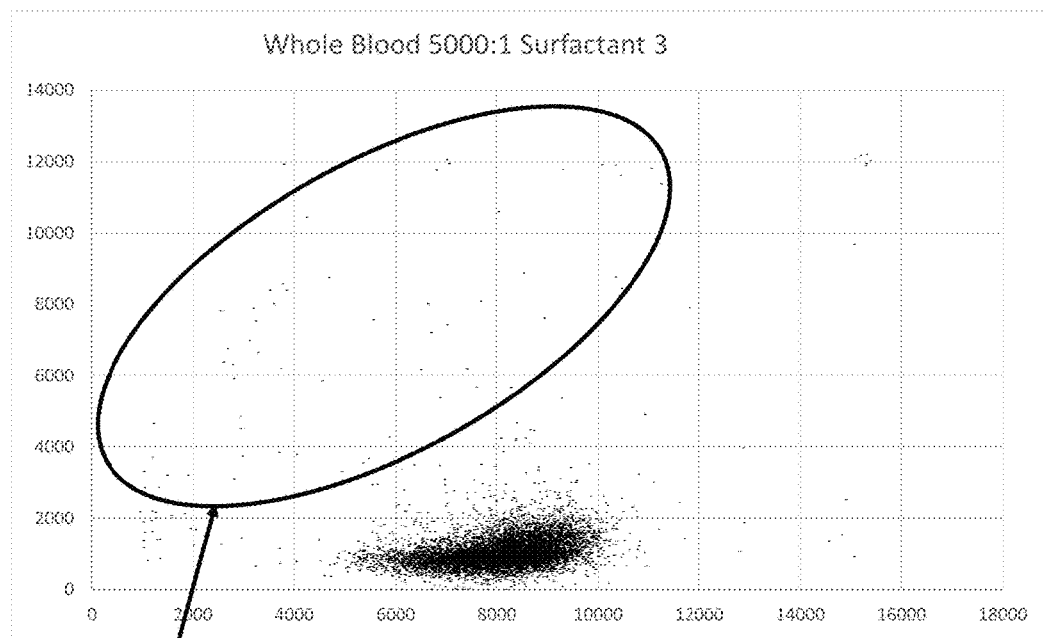
Figure 29:
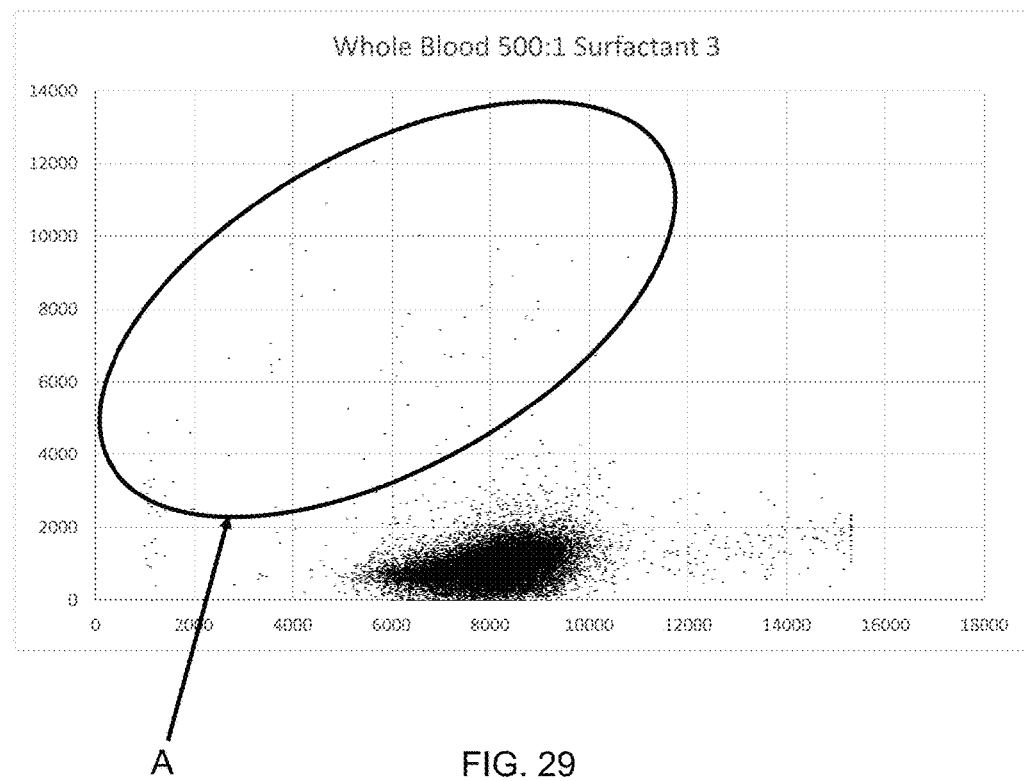
Figure 30:
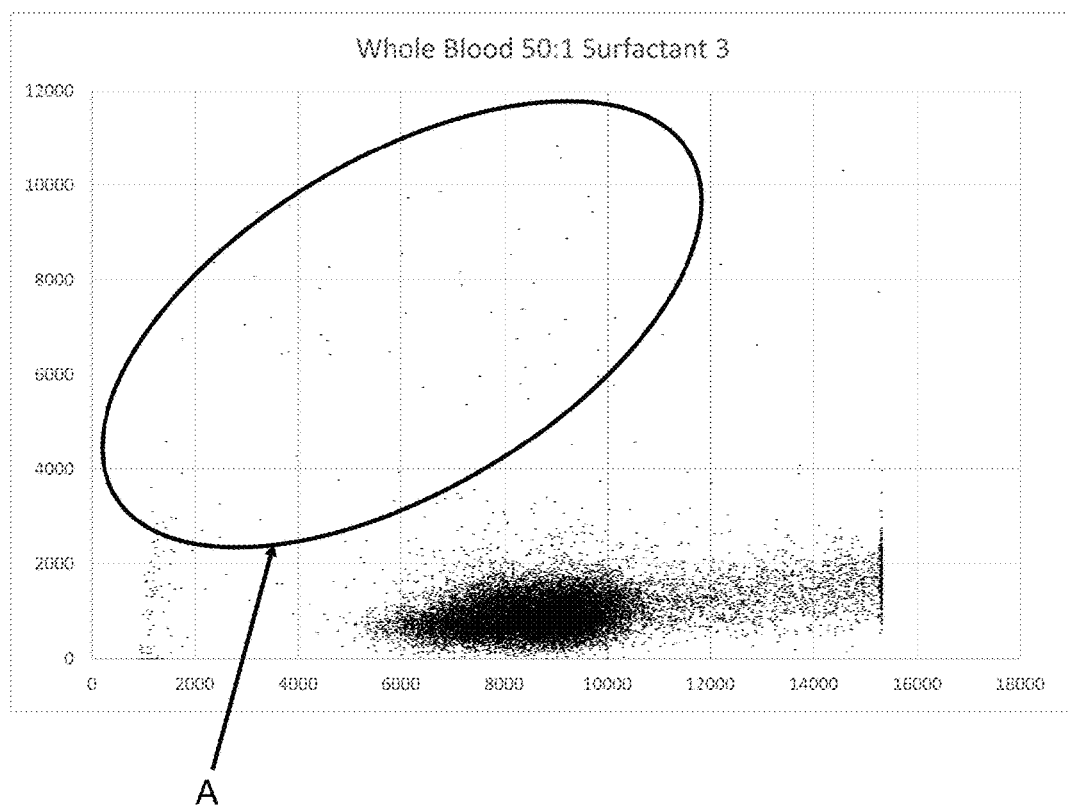

FIGS. 16, 17, and 18 are overlays of FIGS. 12, 13, and 14 with FIG. 15 and demonstrate the RBC and WBC regions are distinct, regardless of whether the RBC are sphered as in FIGS. 12 and 13 or in native disc form as in FIG. 14.

FIGS. 19-30 are four series of scatterplots for blood samples diluted into various media, including just buffered saline, with the WBC region indicated by circle labeled "A." FIGS. 19-30 illustrate that regardless of whether the RBC are sphered or not, the separation of RBC and WBC is insensitive to high RBC coincidence rate.

Figure 31:
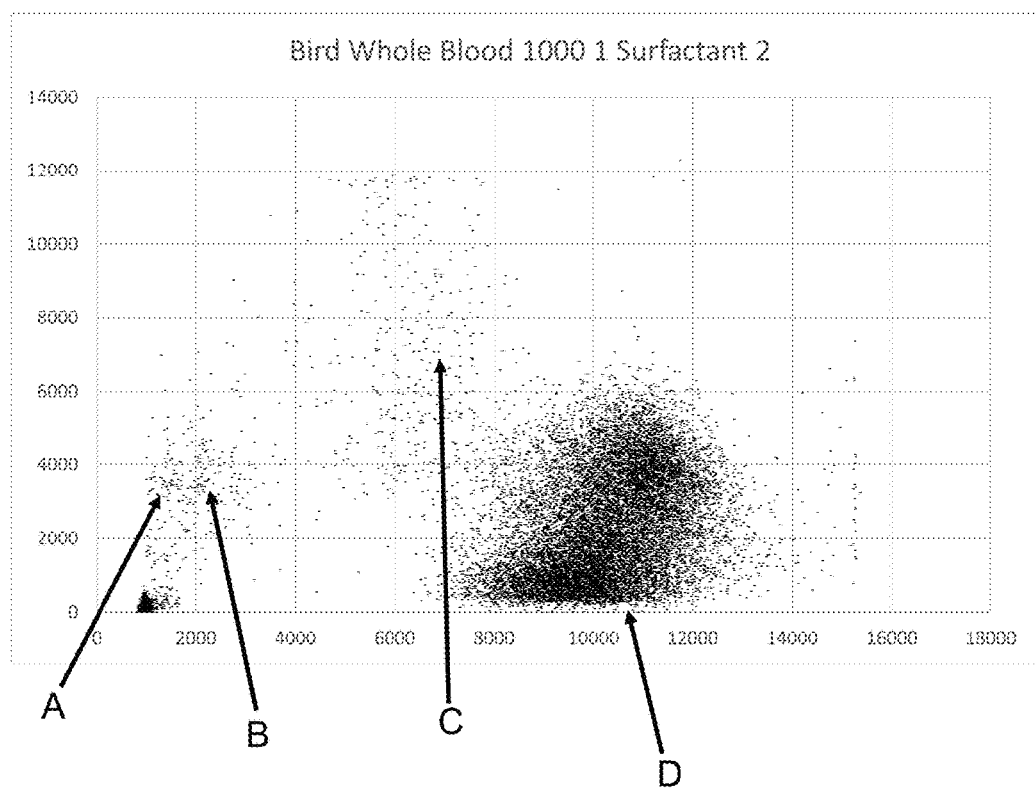
FIG. 31 is a scatterplot of a bird whole blood sample that shows that the RBCs, PLTs (Thrombocytes), and WBCs are distinct.

FIG. 31 is a scatterplot for a bird whole blood sample illustrating: (A) thrombocytes; (B) lymphocytes; (C) polymorphonuclear (PMN) cells; and (D) RBCs. FIG. 31 illustrates that RBC, WBC and thrombocyte populations are distinct. In this context, bird thrombocytes are much larger than human thrombocytes and less numerous. Also they are similar in size to bird lymphocytes. Due to their large size, the bird thrombocytes do appear on the scatterplot. They form a distinct population from the lymphocytes. The other WBC cell types from a distinct group from the RBC. Bird RBC are nucleated ovalocytes. This scatterplot demonstrates that the method distinguishes between nucleated RBC and nucleated WBC based on RBC hemoglobin absorption.

Figure 32A:
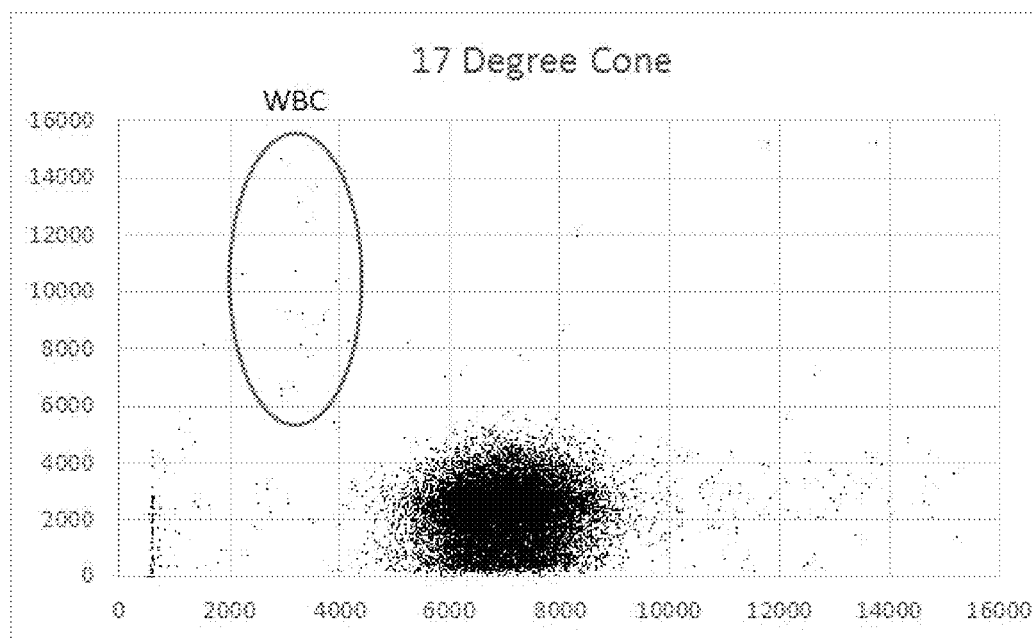
FIGS. 32A, 32B and 32C are three scatterplots of a 1000-fold dilution of a human whole blood sample in a medium that spheres RBCs. The WBC signals decrease in intensity along the absorption axis as the collection cone angle increases.
Figure 32B:
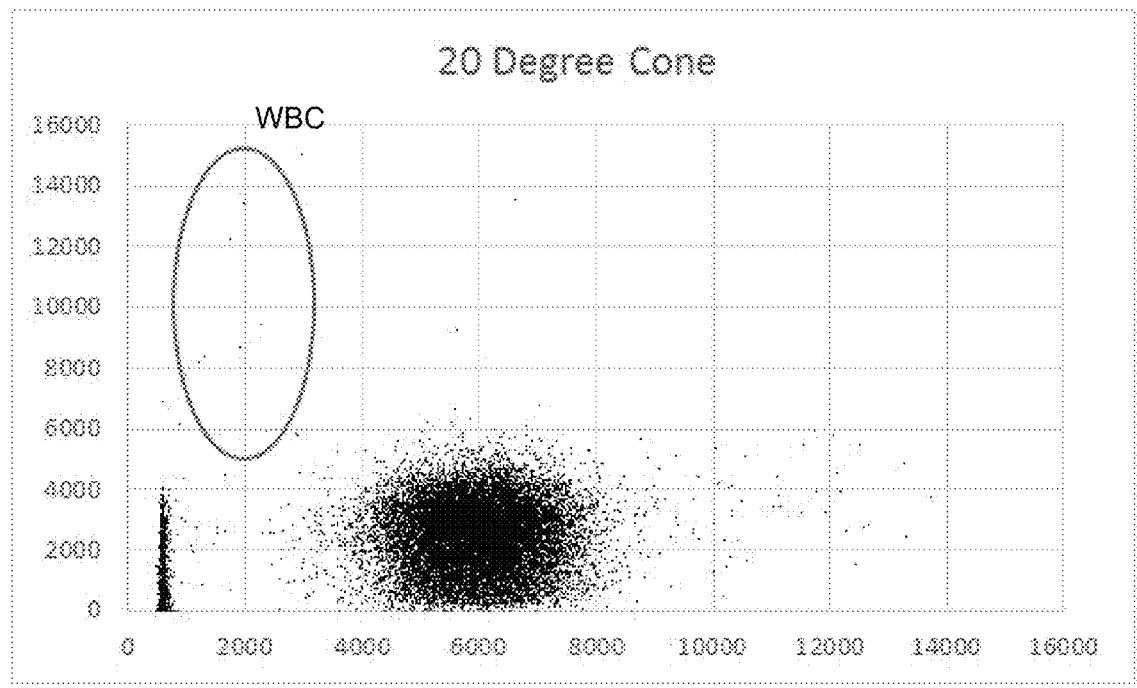
Figure 32C:
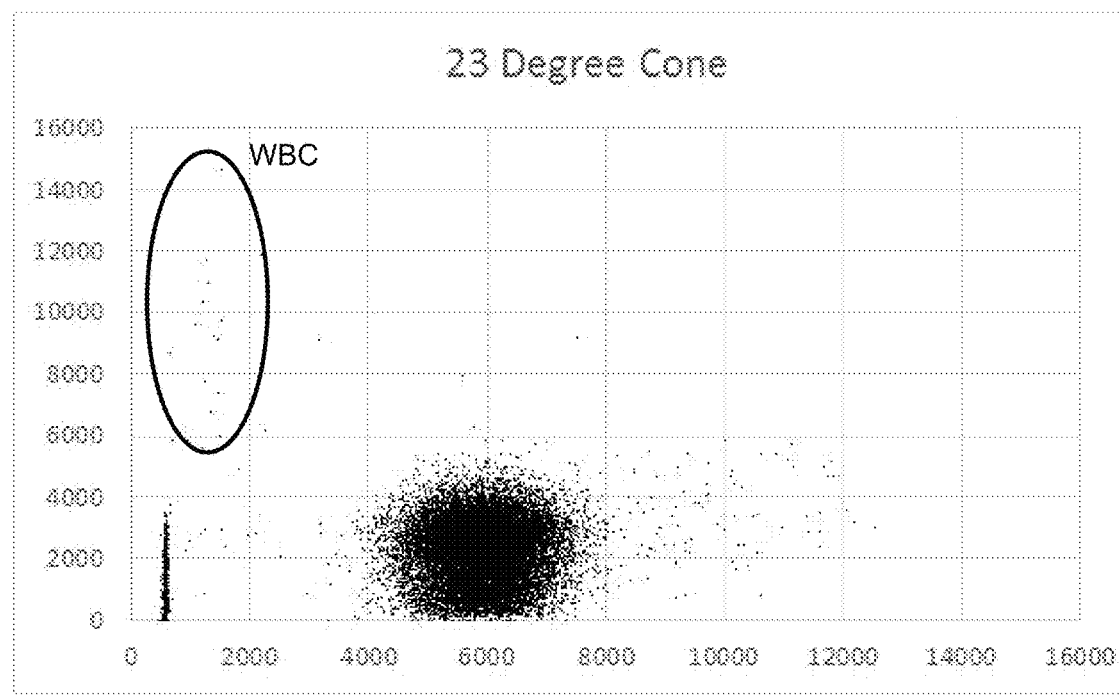

FIGS. 32A, 32B and 32C are three scatterplots of a 1000-fold dilution of a human whole blood sample in a medium that spheres RBCs. The WBC signals, indicated by the encircled region labeled "WBC," decrease in intensity along the absorption axis as the collection cone angle increases. This demonstrates that WBCs scatter almost all incident light within a 23 degree cone, and that the discrimination of WBC from PLT improves as the cone angle increases. For these measurements, the absorption channel detector optics were altered to remove the lensing between the flowcell and the detector to allow for the collection angle to be easily adjusted without reference to focusing conditions. The detector was mounted on a movable micrometer stage to change the distance from the detector to the flowcell and thereby alter the cone angle collected.

Figure 33:
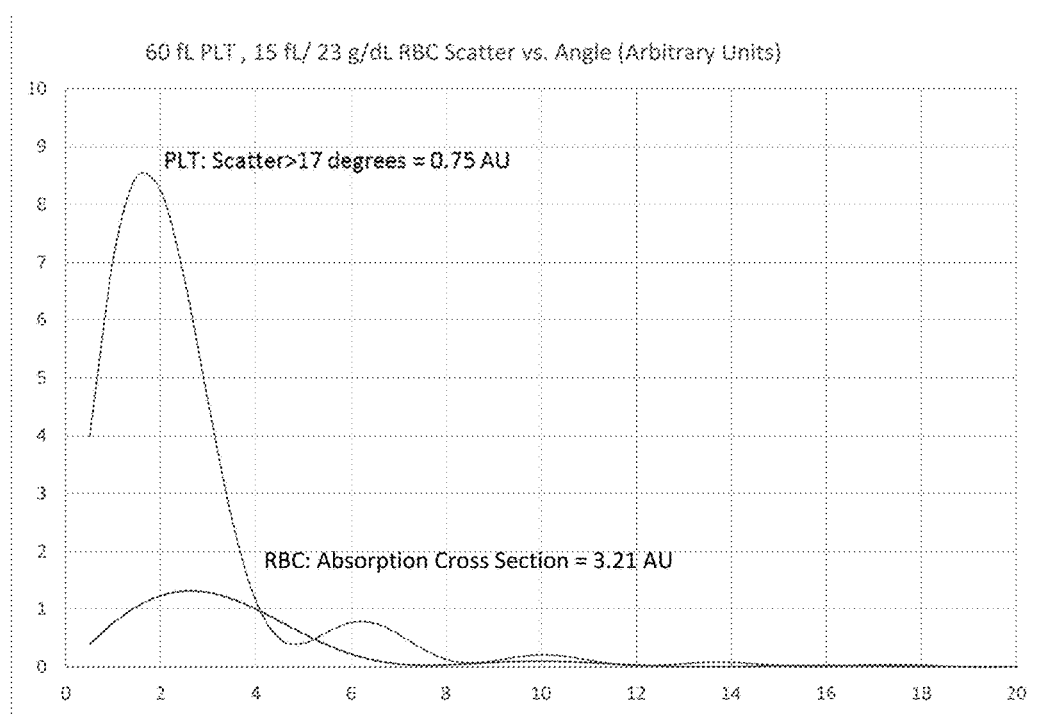
FIG. 33 illustrates the 0-20 degree scatter, absorption and PLT scatter outside 17 degrees to demonstrate for 60 FL PLT and 15 fL/23 g/dL RBC to show that the 17 degree signal for even very microcytic, hypochromic RBC is more than 4 times larger than the signal for very large PLT.

FIG. 33 illustrates the 0-20 degree scatter, absorption and PLT scatter outside 17 degrees to demonstrate for 60 FL PLT and 15 fL/23 g/dL RBC to show that the 17 degree signal for even very microcytic, hypochromic RBC is more than four times larger than the signal for large PLT.

Figure 37:
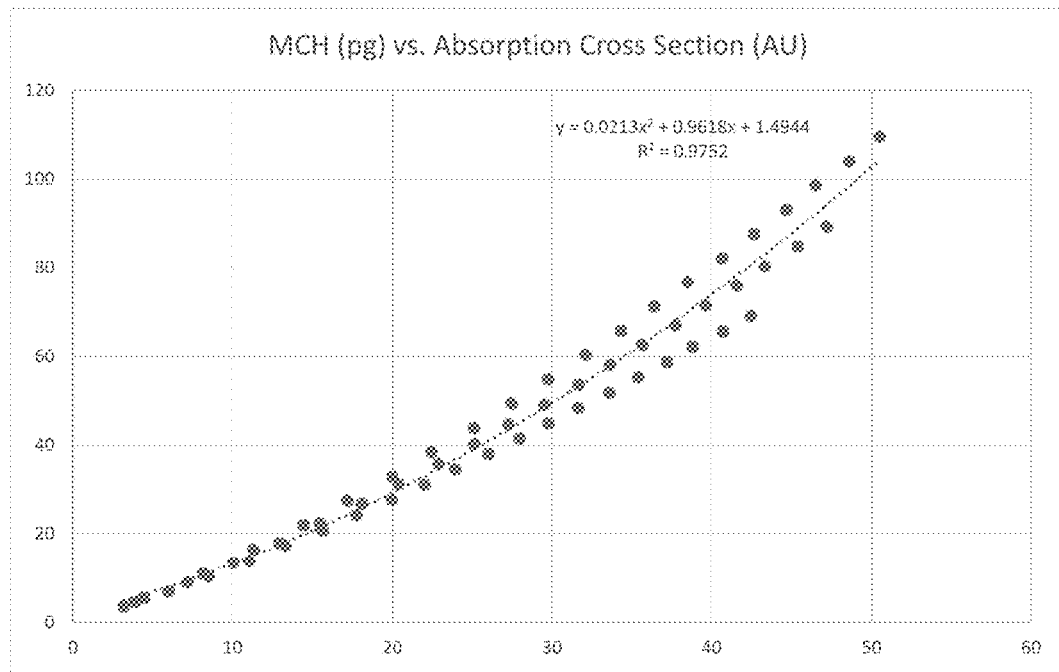
FIG. 37 is a graph of the relationship between absorption cross section and MCH over this range, including a correlation equation and correlation coefficient.
Figure 38:
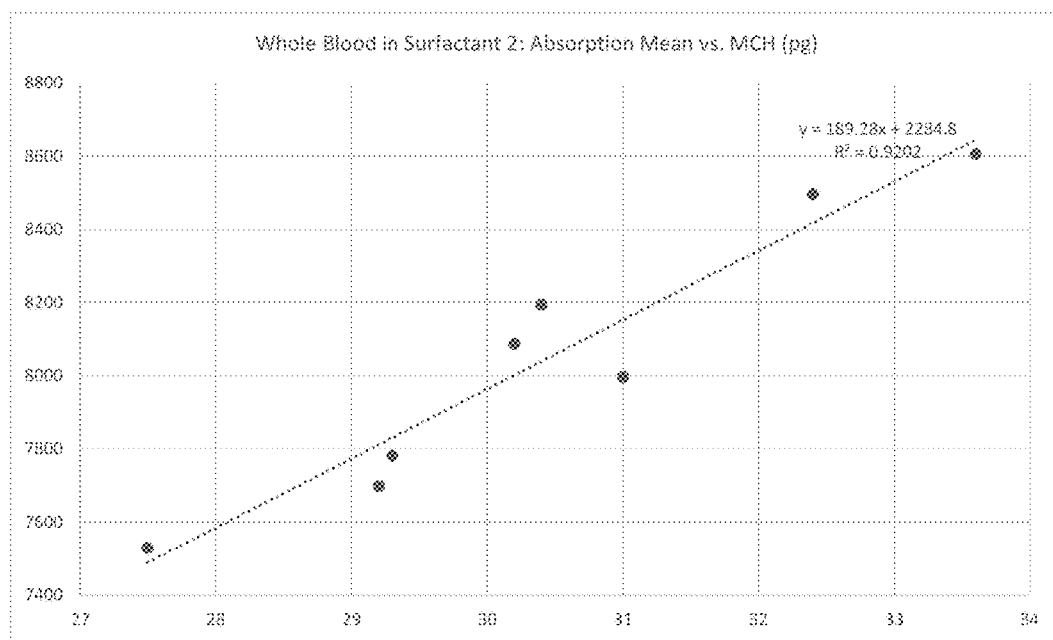
FIG. 38 is a graph of the relationship of RBC Absorption values (17 degree channel) vs. MCH as reported by a commercial hematology analyzer for 8 normal human whole blood samples.

FIGS. 34, 35 and 36 are tables of Absorption Cross Sections for RBCs ranging from 15 fL/23 g/dL to 300 fL/36.5 g/dL. The tables in FIGS. 34, 35 and 36 and the graphical representation of same indicate that absorption cross section is correlated to MCH over the range of RBC volumes of 15 fl-300 fL and MCHC of 23 g/dL-36.5 g/dL, which covers almost all chordate RBCs. FIG. 37 shows that the absorption channel signals obtained for human RBC in whole blood correlate strongly to the theoretical absorption cross section based on MCV and MCHC values for the samples obtained on a commercial hematology analyzer, Abacus 3C™. FIG. 38 shows that the absorption signal obtained correlates to the MCH values obtained for these samples on the Abacus 3C™. This demonstrates that the absorption measurement made using the 17 degree cone scattering detector can be used to determine MCH. By extension, a knowledge of the suspension concentration and the number of cells counted will provide HGB.

FIG. 37 is a graph of the relationship between absorption cross section and MCH over this range, including a correlation equation and correlation coefficient.

FIG. 38 is a graph of the relationship of RBC Absorption values (17 degree channel) vs. MCH as reported by a commercial hematology analyzer for 8 normal human whole blood samples.

Figure 39:
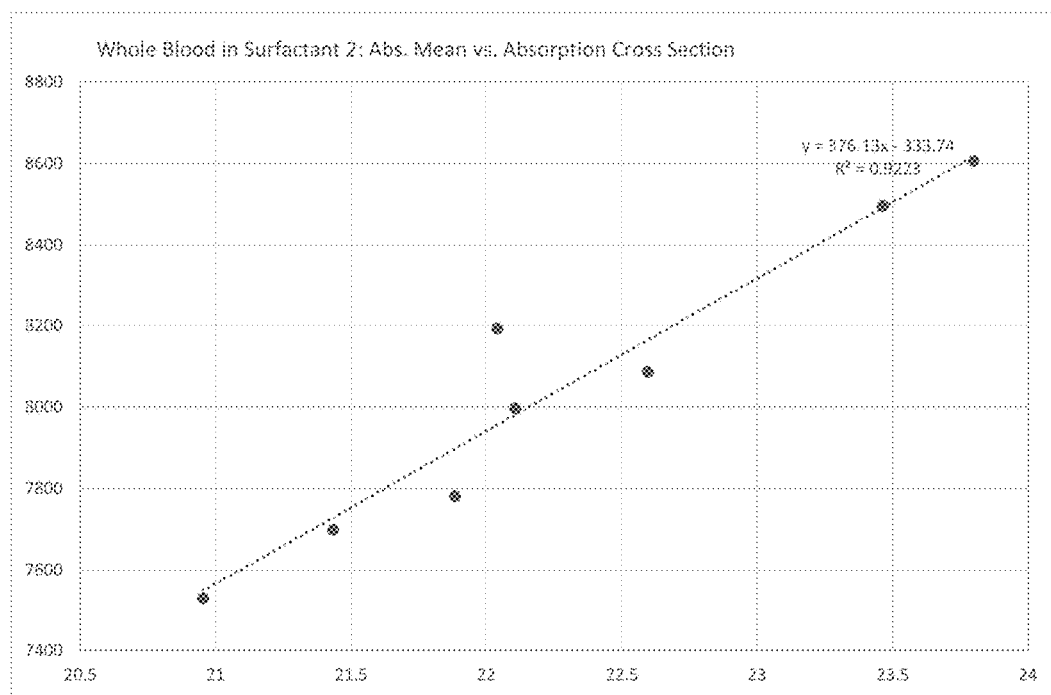
FIG. 39 is a graph of the absorption values vs. theoretical Absorption cross sections based on reported MCV and MCHC.

FIG. 39 is a graph of the absorption values vs. theoretical Absorption cross sections based on reported MCV and MCHC.

FIG. 40 illustrates exemplary parameters of the method and system 100 described herein.

Exemplary Experimental Procedure

A whole blood sample was added to an anticoagulant, such as $K_3$EDTA, mixed, and presented to an aspiration point. Within two seconds, a 20-150 micoliter aliquot of blood was aspirated and 15 microliters of the aliquot were apportioned to be diluted 100-fold into a suspension medium to a total volume of 1.5 mL by dispensing the aliquot and 1.485 mL of suspending medium into a 2.5 mL reaction chamber.

The suspension remained in the chamber for six seconds before 50 microliters were drawn within two seconds and subsequently passed through a flow cell using a displacement pump for cell counting. The 50 microliter cell suspension passed through a quartz flowcell with a 125×125 micron channel, where the cell suspension core stream was hydrodynamically focused by the same medium as used for the cell suspension in a manner that narrows the core stream to a diameter of 10 microns. This utilized 7.712 mL of sheath. 1.0 microliter per second was drawn through the flowcell for a total of 50 seconds. The flow rate under these conditions was 12.66 meters/second.

For a normal human whole blood sample with an RBC count of 5,000,000/microliter, a PLT count of 250,000/microliter and a WBC count of 7,000/microliter, 2,500,000 RBCs, 125,000 PLTs, and 3,500 WBCs would be counted, which is sufficient to provide adequately precise RBC, PLT, and WBC counts. Each cell interrupted a beam of light of about 406 nm wavelength focused at the center of the 125 micron squared channel and two detectors were positioned to collect signals; one collecting light scattered between 75 degrees and 105 degrees, and the other collecting a 17 degree cone of light centered about the direction of light incidence. The three cell types were counted and mutually distinguished based on the positions of their side scatter vs. absorption signals. Following the 50 second counting cycle, 5 mL of the same suspension medium was used to rinse the syringes, transmission lines, reaction chamber, and flowcell for period of 10 seconds. During this 10 seconds, subsequent samples were aspirated into the system for counting. The total cycle time was 70 seconds for the first sample and 60 seconds for every sample thereafter. The total reagent usage was 14.2 mL per sample.

While embodiments of the invention have been shown and described with reference to certain embodiments thereof, it will be understood by those skilled in the art that various changes in form and details may be made therein without departing from the spirit and scope of the invention as defined by the appended claims and equivalents thereof.

The invention claimed is:

1. A method for measuring concentrations of blood cell components, the method comprising:
 obtaining a blood sample from a subject, the blood sample comprising nucleated red blood cells (NRBCs), white blood cells (WBCs) and platelets (PLTs);

mixing the blood sample with a non-lysing aqueous solution to form a sample mixture comprising a predetermined tonicity;
passing the sample mixture through a flow cell;
emitting light towards the flow cell;
measuring an amount of light absorbed by the NRBCs;
measuring an amount of light scattered by WBCs and PLTs; and
determining a concentration of each of the NRBCs, WBCs and PLTs present in the sample mixture based on the measured amount of light absorbed by the NRBCs and scattered by the WBCs and PLTs,
wherein the sample mixture does not comprise a dye.

2. The method according to claim 1, further comprising:
measuring an amount of light side-scattered by the NRBCs, WBCs and PLTs.

3. The method according to claim 1, wherein the NRBCs are present in the sample mixture when the amount of light scattered by the WBCs is measured, and wherein the WBCs are present in the sample mixture when the amount of light absorbed by the NRBCs is measured.

4. The method according to claim 1, wherein the subject is a chordate.

5. The method according to claim 1, wherein the non-lysing aqueous solution converts oxyhemoglobin present in the sample mixture to methemoglobin while substantially maintaining the predetermined tonicity.

6. The method according to claim 5, wherein the non-lysing aqueous solution comprises a reagent that converts oxyhemoglobin to methemoglobin.

7. The method according to claim 5, wherein the predetermined tonicity is 260-330 milliosmolar (mOsm).

8. The method according to claim 1, further comprising determining at least one of a mean cellular hemoglobin (MCH) and a total hemoglobin (HGB) concentration by the amount of light absorbed by the RBCs using a single absorbance detector.

9. The method according to claim 1, wherein the light emitted towards the flow cell is at a wavelength of from about 400 nm to about 440 nm.

10. The method according to claim 1, wherein the aqueous solution comprises a reagent used as a diluent for the blood sample, a flow cytometric sheathing fluid for the diluted blood sample mixture, and a rinsing solution for the diluted blood sample mixture.

11. The method according to claim 10, wherein the reagent comprises water-soluble salts.

12. The method according to claim 10, wherein the reagent comprises water-soluble salts and one or more surfactants.

13. A method for measuring concentrations of blood cell components, the method comprising:
obtaining a blood sample from a subject, the blood sample comprising red blood cells (RBCs), white blood cells (WBCs) and platelets (PLTs);
mixing the blood sample with a non-lysing aqueous solution to form a sample mixture comprising a predetermined tonicity;
passing the sample mixture through a flow cell;
emitting light towards the flow cell;
measuring an amount of light absorbed by the RBCs;
measuring an amount of light scattered by WBCs and PLTs; and
determining a concentration of each of the RBCs, WBCs and PLTs present in the sample mixture based on the measured amount of light absorbed by the RBCs and scattered by the WBCs and PLTs,
wherein the non-lysing aqueous solution converts oxyhemoglobin present in the sample mixture to methemoglobin.

14. The method according to claim 13, further comprising:
measuring an amount of light side-scattered by the RBCs, WBCs and PLTs.

15. The method according to claim 13, wherein the RBCs are present in the sample mixture when the amount of light scattered by the WBCs is measured, and wherein the WBCs are present in the sample mixture when the amount of light absorbed by the RBCs is measured.

16. The method according to claim 13, wherein the RBCs in the blood sample comprise nucleated red blood cells (NRBCs).

17. The method according to claim 16, further comprising:
measuring an amount of light absorbed by the NRBCs;
determining a concentration of the NRBCs present in the sample mixture based on the measured amount of light absorbed by the NRBCs and scattered by the WBCs and PLTs.

18. The method according to claim 13, further comprising determining at least one of a mean cellular hemoglobin (MCH) and a total hemoglobin (HGB) concentration based on the amount of light absorbed by the RBCs using a single absorbance detector.

19. The method according to claim 13, wherein the light emitted towards the flow cell is at a wavelength of from about 400 nm to about 440 nm.

20. The method according to claim 13, wherein the subject is a human and the blood sample comprises human red blood cells (HRBCs), human white blood cells (HWBCs) and human platelets (HPLTs), the method further comprising distinguishing between the HRBCs and the HPLTs across a human physiologic range of RBC sizes of about 15 fL to about 180 fL and a human physiologic range of PLT sizes of about 1 fL to about 60 fL.

21. The method according to claim 20, further comprising distinguishing between the H RBCs and the H PLTs across a human physiologic range of component concentrations of about 1000/microliter to about 1,500,000/microliter of PLTs and of about 250,000/microliter to about 7,000,000/microliter of RBCs.

22. The method according to claim 13, wherein the sample mixture comprises at least one surfactant comprising one of polyoxyethylene lauryl ether and sodium dodecyl sulfate to sphere the RBCs.

23. The method according to claim 13, further comprising detecting light absorbed by the RBCs in the sample mixture in the flow cell by a single absorption detector.

24. The method according to claim 13, wherein the amount of light absorbed by the RBCs is detected by an absorption detector within a first cone of a first predetermined number of degrees around the incident light.

25. The method according to claim 24, wherein the first predetermined number of degrees is from about 17 to about 26 degrees.

26. The method according to claim 24, further comprising:
measuring an amount light side-scattered by the RBCs, WBCs and PLTs outside the first cone and within a second cone of a second predetermined number of degrees around the incident light.

27. The method according to claim 26, wherein the second predetermined number of degrees around the incident light is from about 75 degrees to about 105 degrees.

\* \* \* \* \*